(12) United States Patent
Inouye et al.

(10) Patent No.: US 11,944,314 B2
(45) Date of Patent: Apr. 2, 2024

(54) LEFT ATRIAL APPENDAGE IMPLANT WITH CONTINUOUS COVERING

(71) Applicant: BOSTON SCIENTIFIC SCIMED, INC., Maple Grove, MN (US)

(72) Inventors: Joshua Mark Inouye, Maple Grove, MN (US); James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/929,652

(22) Filed: Jul. 15, 2020

(65) Prior Publication Data

US 2021/0015491 A1    Jan. 21, 2021

Related U.S. Application Data

(60) Provisional application No. 62/875,040, filed on Jul. 17, 2019.

(51) Int. Cl.
*A61B 17/12* (2006.01)
*A61B 17/00* (2006.01)
*A61B 90/00* (2016.01)

(52) U.S. Cl.
CPC .. *A61B 17/12122* (2013.01); *A61B 17/12172* (2013.01); *A61B 2017/00632* (2013.01);
(Continued)

(58) Field of Classification Search
CPC ........ A61B 17/12122; A61B 17/12172; A61B 17/12031; A61B 17/12177; A61B 17/0057; A61B 17/12109; A61B 2017/00632; A61B 2017/1205; A61B 2017/12054; A61B 2017/00597; A61B 2017/0061;
(Continued)

(56) References Cited

U.S. PATENT DOCUMENTS 178,283 A    6/1876  French
1,967,318 A  7/1934  Monahan
(Continued)

FOREIGN PATENT DOCUMENTS

CN    1399571 A     2/2003
CN    202143640 U   2/2012
(Continued)

OTHER PUBLICATIONS

International Search Report and Written Opinion dated Aug. 3, 2004 for International Application No. PCT/US2004/008109.
(Continued)

*Primary Examiner* — Ashley L Fishback
*Assistant Examiner* — Chima U Igboko
(74) *Attorney, Agent, or Firm* — Seager, Tufte & Wickhem LLP

(57) ABSTRACT

An implant for occluding a left atrial appendage may include an expandable framework configured to shift between a collapsed configuration and an expanded configuration, wherein the expandable framework includes an attachment point configured to secure the expandable framework to a delivery device, and an occlusive element disposed on a proximal portion of the expandable framework, wherein the occlusive element covers the attachment point.

10 Claims, 20 Drawing Sheets

(52) U.S. Cl.
CPC ............... *A61B 2017/1205* (2013.01); *A61B 2017/12054* (2013.01); *A61B 2090/3966* (2016.02)

(58) Field of Classification Search
CPC .......... A61B 2017/00615; A61B 2017/00575; A61B 2017/00243; A61B 2090/3966; A61F 2/2436; A61F 2/2442; A61F 2/2466; A61F 2/95; A61F 2/2427; A61F 2/011
USPC ........................................................ 606/200
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |

(56) References Cited

U.S. PATENT DOCUMENTS

| | | |
|---|---|---|
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |

(56) References Cited

U.S. PATENT DOCUMENTS

| | | |
|---|---|---|
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,211,124 B2 | 12/2015 | Campbell et al. |
| 9,445,895 B2 | 9/2016 | Kreidler |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,629,636 B2 | 4/2017 | Fogarty et al. |
| 9,730,701 B2 | 8/2017 | Tischler et al. |
| 9,883,936 B2 * | 2/2018 | Sutton ............... A61B 17/0057 |
| 9,883,963 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0220667 A1 | 11/2003 | van der Burg et al. |
| 2004/0034366 A1 | 2/2004 | van der Burg et al. |
| 2004/0044361 A1 | 3/2004 | Frazier et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |

(56) References Cited

U.S. PATENT DOCUMENTS

| | | |
|---|---|---|
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0009800 A1* | 1/2006 | Christianson ...... A61B 17/0057 606/213 |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0135826 A1* | 6/2007 | Zaver ............... A61B 17/12172 606/157 |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0259295 A1* | 10/2009 | Rust .................. A61F 2/95 623/1.23 |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1* | 2/2012 | Khairkhahan ..... A61B 17/0057 606/194 |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0316584 A1* | 12/2012 | Miles ................ A61B 17/0057 606/157 |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0090684 A1* | 4/2013 | Van Bladel ........ A61B 17/0401 606/213 |
| 2013/0110154 A1 | 5/2013 | van der Burg et al. |
| 2013/0165735 A1 | 6/2013 | Khairkhahan et al. |
| 2013/0211492 A1 | 8/2013 | Schneider et al. |
| 2013/0331884 A1 | 12/2013 | Van der Burg et al. |
| 2014/0005714 A1* | 1/2014 | Quick ............. A61B 17/12031 606/200 |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0181751 A1 | 6/2017 | Larsen et al. |
| 2017/0340336 A1 | 11/2017 | Osypka |
| 2018/0064446 A1 | 3/2018 | Figulla et al. |
| 2018/0070950 A1 | 3/2018 | Zaver et al. |
| 2018/0116678 A1* | 5/2018 | Melanson ........ A61B 17/12122 |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2018/0310925 A1* | 11/2018 | Inouye ............. A61B 17/12172 |
| 2019/0021711 A1* | 1/2019 | Li ..................... A61B 17/0057 |
| 2019/0059876 A1* | 2/2019 | Decker ................ A61B 17/068 |
| 2019/0083075 A1* | 3/2019 | Onushko .......... A61B 17/12122 |
| 2019/0090884 A1* | 3/2019 | Bowman .......... A61B 17/12172 |
| 2019/0090885 A1* | 3/2019 | Zhou .............. A61B 17/12031 |
| 2019/0183512 A1* | 6/2019 | Subramaniam .. A61B 17/12145 |
| 2019/0209178 A1* | 7/2019 | Richter ............. A61B 17/12172 |
| 2019/0209180 A1* | 7/2019 | Kealey ............. A61B 17/0057 |
| 2019/0223883 A1 | 7/2019 | Anderson et al. |
| 2019/0374229 A1* | 12/2019 | Anderson ........ A61B 17/12172 |
| 2020/0107836 A1* | 4/2020 | O'Halloran ...... A61B 17/12136 |
| 2020/0121324 A1* | 4/2020 | O'Halloran .......... A61B 5/0261 |
| 2020/0187952 A1* | 6/2020 | Walsh .............. A61B 17/12113 |
| 2020/0253613 A1* | 8/2020 | Pan ................. A61B 17/12122 |
| 2020/0390428 A1* | 12/2020 | Lee ................. A61B 17/12163 |

FOREIGN PATENT DOCUMENTS

| | | |
|---|---|---|
| CN | 106859722 A | 6/2017 |
| DE | 10201004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |

(56) References Cited

FOREIGN PATENT DOCUMENTS

| | | |
|---|---|---|
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al., "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 20, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.
International Search Report and Written Opinion dated Oct. 23, 2020 for International Application No. PCT/US2020/042192.

* cited by examiner

LEFT ATRIAL APPENDAGE IMPLANT WITH CONTINUOUS COVERING

CROSS-REFERENCE TO RELATED APPLICATIONS

This application claims the benefit of priority of U.S. Provisional Application No. 62/875,040 filed Jul. 17, 2019, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

The occurrence of thrombi in the left atrial appendage during atrial fibrillation may be due to stagnancy of the blood pool in the left atrial appendage. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex with large irregular surface areas and a narrow ostium or opening compared to the depth of the left atrial appendage. These aspects as well as others, taken individually or in various combinations, may lead to high flow resistance of blood out of the left atrial appendage and/or formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Over time, exposed surface(s) of an implant spanning the left atrial appendage may become covered with tissue (a process called endothelization), effectively removing the left atrial appendage from the circulatory system and reducing or eliminating the amount of thrombi which may enter the blood stream from the left atrial appendage. Of the known medical devices and methods, each has certain advantages and disadvantages. There is an ongoing need to provide alternative medical devices and introducers as well as alternative methods for manufacturing and using medical devices and introducers.

SUMMARY

In a first aspect, an implant for occluding a left atrial appendage may comprise an expandable framework configured to shift between a collapsed configuration and an expanded configuration, wherein the expandable framework includes an attachment point configured to secure the expandable framework to a delivery device; and an occlusive element disposed on a proximal portion of the expandable framework, wherein the occlusive element covers the attachment point.

In addition or alternatively, the expandable framework includes a proximal hub.

In addition or alternatively, the attachment point is a pin extending laterally across the proximal hub.

In addition or alternatively, the implant may further include a fastening element securing the occlusive element to the pin.

In addition or alternatively, the implant may further include a plurality of anchor members configured to secure the implant to tissue within the left atrial appendage.

In addition or alternatively, the occlusive element includes a porous mesh.

In addition or alternatively, a system for occluding a left atrial appendage may comprise a delivery device including an outer sheath and an inner elongate member slidably disposed within a lumen of the outer sheath, and an implant configured to occlude the left atrial appendage. The implant may comprise an expandable framework configured to shift between a collapsed configuration when disposed within the outer sheath and an expanded configuration when disposed outside of the outer sheath, wherein the expandable framework includes an attachment point configured to secure the expandable framework to the delivery device; and an occlusive element disposed on a proximal portion of the expandable framework, wherein the occlusive element covers the attachment point.

In addition or alternatively, the system may further include a tether extending longitudinally within the inner elongate member, the tether engaging the attachment point in a delivery configuration.

In addition or alternatively, the tether extends through the occlusive element in the delivery configuration.

In addition or alternatively, the tether is disengaged from the attachment point in a released configuration.

In addition or alternatively, the system may further comprise a release mechanism disposed within the lumen of the inner elongate member, wherein the release mechanism is configured to sever the tether within the lumen of the inner elongate member.

In addition or alternatively, the release mechanism includes a cutting blade disposed within the inner elongate member.

In addition or alternatively, the system may further comprise a turnstile movably engaged with a proximal end of the inner elongate member.

In addition or alternatively, the attachment point may include a cam member extending laterally across a proximal hub of the expandable framework. The cam member may be configured to cooperate with a distal end of the inner elongate member.

In addition or alternatively, the tether extends around the cam member, such that axial translation of the tether is configured to angle the expandable framework relative to a central longitudinal axis of the delivery device.

In addition or alternatively, a method of occluding a left atrial appendage may comprise: advancing an implant configured to occlude the left atrial appendage into the left atrial appendage, wherein the implant comprises an expandable framework configured to shift between a collapsed configuration and an expanded configuration, wherein the expandable framework includes an attachment point configured to secure the expandable framework to a delivery device; and an occlusive element disposed on a proximal portion of the expandable framework, wherein the occlusive element covers the attachment point; deploying the implant within the left atrial appendage; and releasing the implant within the left atrial appendage. After releasing the implant, all metallic materials of the implant may be disposed distal of a proximal-facing surface of the occlusive element.

In addition or alternatively, releasing the implant includes severing a tether securing the implant to the delivery device.

In addition or alternatively, axial translation of the tether prior to severing the tether angles the expandable framework relative to a central longitudinal axis of the delivery device.

In addition or alternatively, rotation of a turnstile relative to a proximal end of the delivery device severs the tether.

In addition or alternatively, subsequent proximal retraction of the turnstile disengages the tether from the implant.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
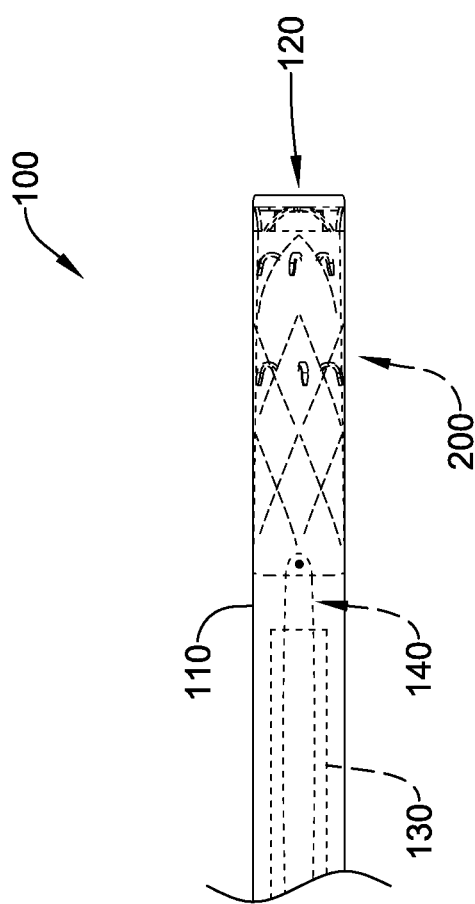
FIGS. 1-2 illustrate aspects of a system and an implant for occluding a left atrial appendage.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, the implant and/or the system could be used in a non-percutaneous procedure. Devices and methods in accordance with the disclosure may also be adapted and configured for other uses within the anatomy.

Figure 2:
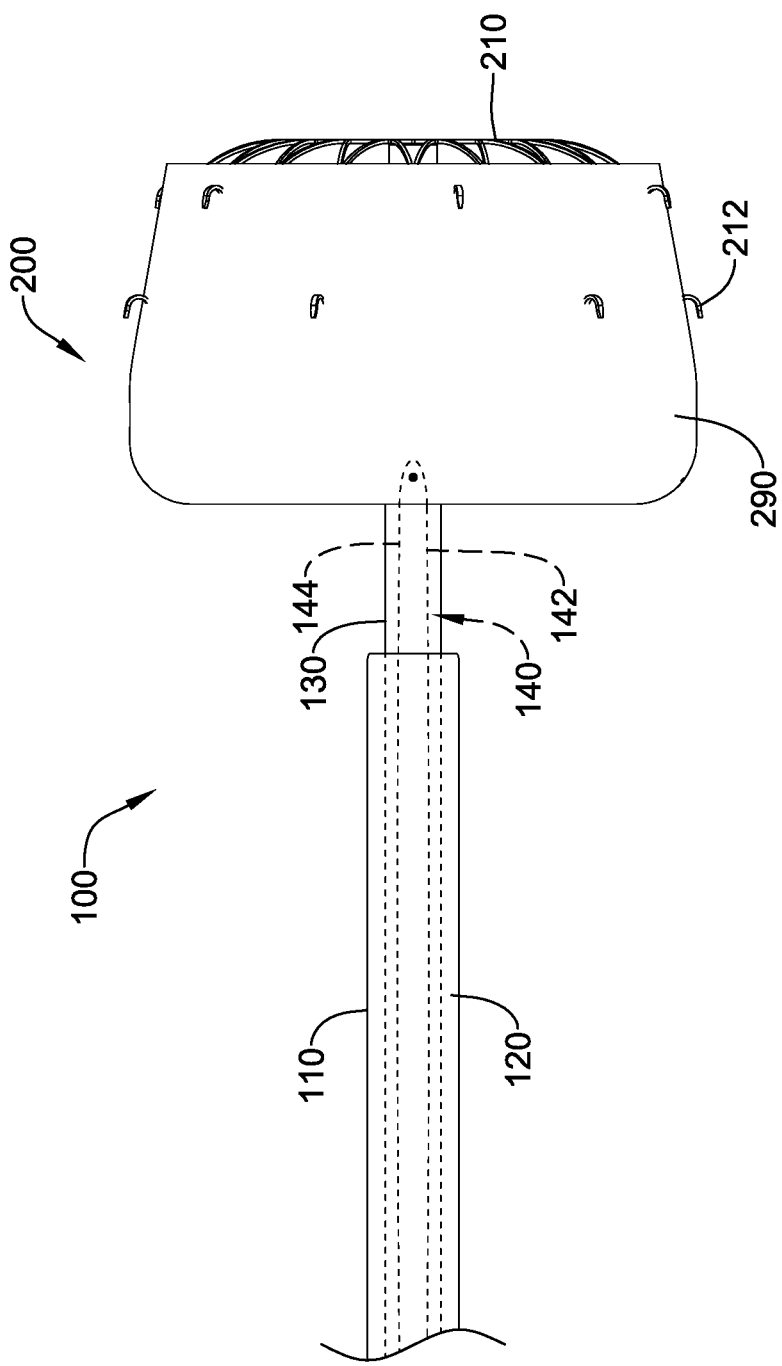
Figure 15:
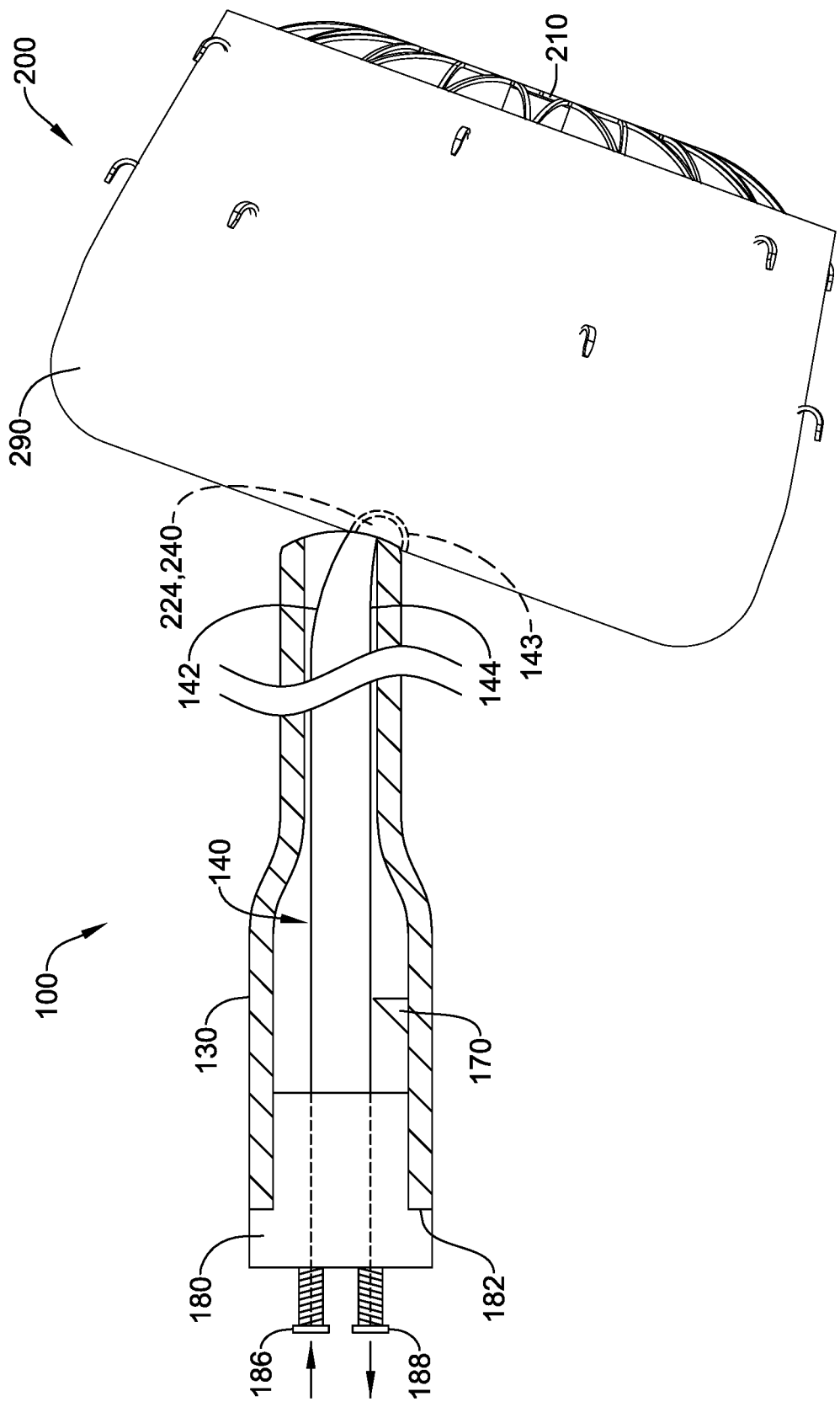
Figure 16:
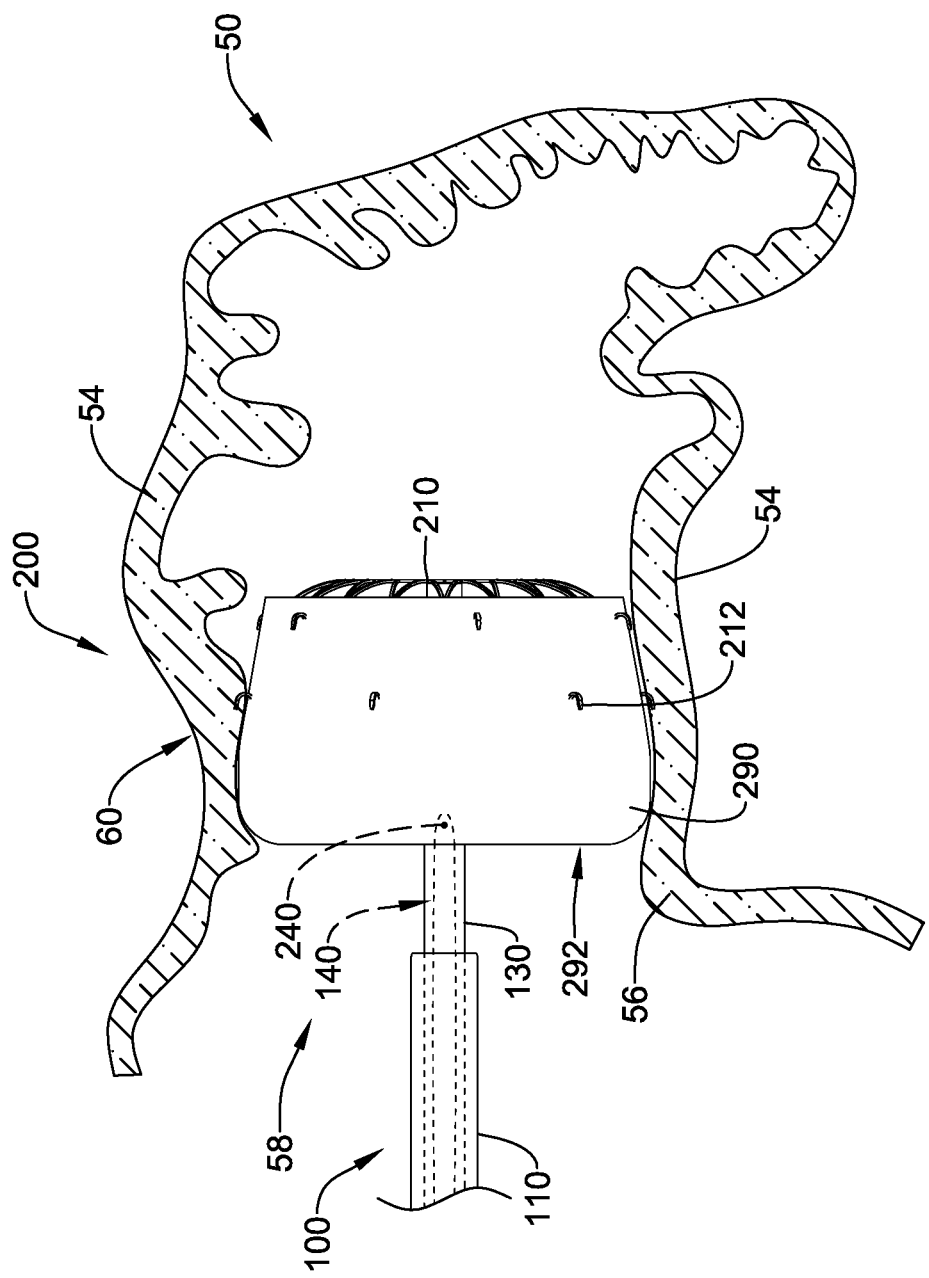
FIGS. 16-18 illustrate selected aspects of a method of deploying and releasing the implant for occluding a left atrial appendage.
Figure 17:
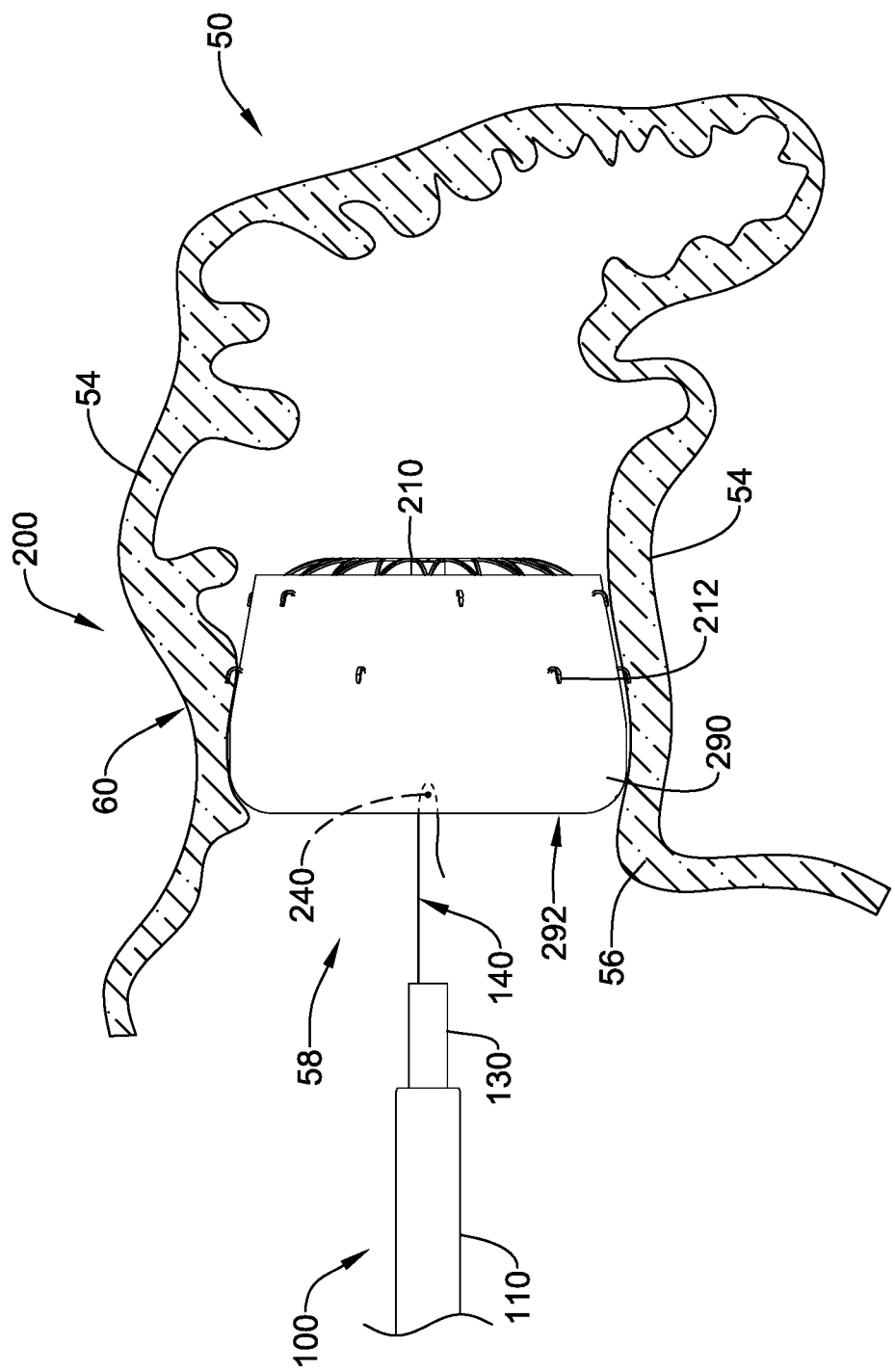

FIGS. 1 and 2 illustrate elements of a system 100 for occluding a left atrial appendage (e.g., FIGS. 15-17). The system 100 may include a delivery device include an outer sheath 110 having a lumen 120 extending to a distal end. The system 100 may include an implant 200 for occluding the left atrial appendage. The implant 200 may comprise an expandable framework 210 configured to shift between a collapsed configuration and an expanded configuration. When the implant 200 is disposed within the lumen 120 of the outer sheath 110, the expandable framework 210 may be held and/or disposed in the collapsed configuration, as shown in FIG. 1 for example. When the implant 200 is disposed outside of the lumen 120 of the outer sheath 110, the expandable framework 210 may be expanded and/or shifted towards and/or into the expanded configuration, as shown in FIG. 2 for example. Some suitable, but non-limiting, examples of materials for the outer sheath 110 are discussed below.

The system 100 and/or the delivery device may include an inner elongate member 130 slidably disposed within the lumen 120 of the outer sheath 110. In some embodiments, the inner elongate member 130 may include a lumen extending axially and/or longitudinally from a proximal end of the inner elongate member 130 to a distal end of the inner elongate member 130. In some embodiments, the inner elongate member 130 may include a plurality of lumens extending axially and/or longitudinally from a proximal end of the inner elongate member 130 to a distal end of the inner elongate member 130. In at least some embodiments, the inner elongate member 130 and/or the outer sheath 110 may include one or more seals and/or sealing structures within the lumen or lumens thereof to reduce and/or prevent fluid (e.g., blood) flow through the lumen or lumens thereof from the distal end to the proximal end. The inner elongate member 130 may be axially and/or longitudinally movable relative to the outer sheath 110. In some embodiments, the inner elongate member 130 may be used to advance (e.g., push) the implant 200 out of the lumen 120 of the outer sheath 110. In some embodiments, the inner elongate member 130 may be used to hold and/or maintain an axial and/or longitudinal position of the implant 200 as the outer sheath 110 is retracted and/or axially translated proximally relative to the implant 200 to expose the implant 200 from the lumen 120 of the outer sheath 110. Some suitable, but non-limiting, examples of materials for the inner elongate member 130 are discussed below.

The system 100 and/or the delivery device may further include a tether 140 extending longitudinally within the lumen (or within at least one of the plurality of lumens) of the inner elongate member 130. In some embodiments, the tether 140 may include a first longitudinally extending portion 142 and a second longitudinally extending portion 144. In some embodiments, the first longitudinally extending portion 142 and/or the second longitudinally extending portion 144 may extend completely through an entire length of the lumen of the inner elongate member 130. In some embodiments, the second longitudinally extending portion 144 may extend along only a portion of the entire length (e.g., less than the entire length) of the lumen of the inner elongate member 130. In some embodiments, the first longitudinally extending portion 142 may extend completely through an entire length of a first lumen of the plurality of lumens of the inner elongate member 130. In some embodiments, the second longitudinally extending portion 144 may extend completely through an entire length of a second lumen of the plurality of lumens of the inner elongate member 130. In some embodiments, the second longitudinally extending portion 144 may extend along only a portion of the entire length (e.g., less than the entire length) of the second lumen of the plurality of lumens of the inner elongate member 130. Some suitable, but non-limiting, examples of materials for the tether 140 are discussed below.

In some embodiments, the implant 200 includes an occlusive element 290 disposed and/or positioned on, over, and/or around at least a portion of the expandable framework 210, as shown in FIG. 2. In at least some embodiments, the occlusive element 290 may be secured to, attached to, and/or connected to the expandable framework 210. In some embodiments, the occlusive element 290 may be secured to, attached to, and/or connected to the expandable framework 210 at a plurality of discrete locations. In some embodiments, the expandable framework 210 may include a plurality of anchor members 212 extending therefrom, the plurality of anchor members 212 being configured to secure the implant 200 and/or the expandable framework 210 to tissue within a left atrial appendage. For example, the plurality of anchor members 212 being configured to engage with a wall of a main body of the left atrial appendage (e.g., FIGS. 16-18). In at least some embodiments, the plurality of anchor members 212 may extend through the occlusive element 290, where the expandable framework 210 and a base portion of each of the plurality of anchor members 212 is disposed on a first side (e.g., an inside) of the occlusive element 290 and a free end or tip of each of the plurality of anchor members 212 is disposed on a second side (e.g., an outside) of the occlusive element 290.

Figure 3:
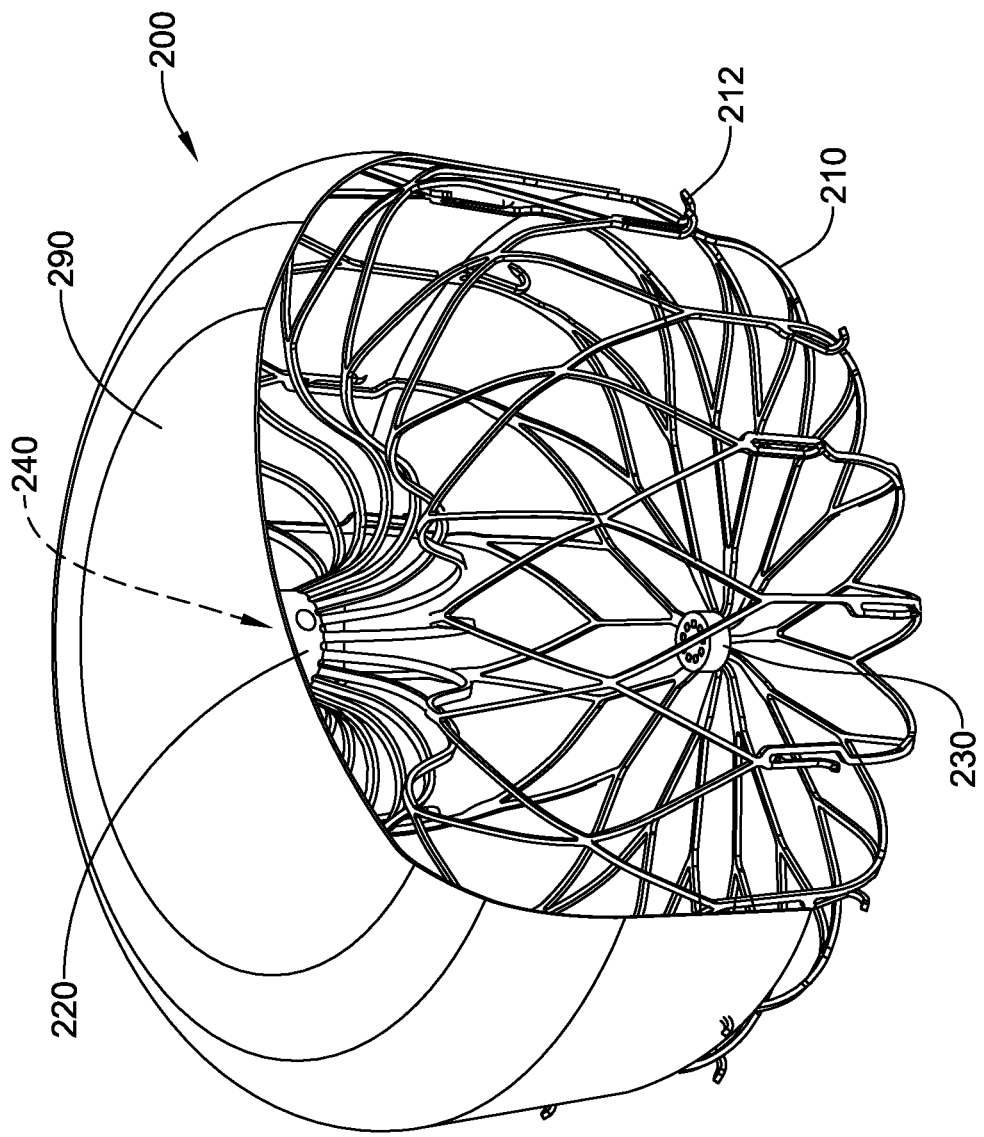
FIG. 3 is a partial cut-away view of the implant for occluding a left atrial appendage.

FIG. 3 illustrates a partial cut-away view of the implant 200, wherein a portion of the occlusive element 290 has been removed to show aspects of the expandable framework 210. In at least some embodiments, the occlusive element 290 may extend across a proximal portion of the expandable framework 210. In some embodiments, the occlusive element 290 may be spaced apart from at least some portions of the proximal portion of the expandable framework 210. The expandable framework 210 may be manually expandable and/or the expandable framework 210 may be configured to self-expand from the collapsed configuration to the expanded configuration when the expandable framework 210 is unconstrained. For example, in some embodiments, the expandable framework 210 may be made from a shape memory material. In some embodiments, the expandable framework 210 may include and/or may be formed from a plurality of interconnected struts and/or frame segments. The base portion of each of the plurality of anchor members 212 may be fixedly attached to the expandable framework 210 and/or the plurality of interconnected struts and/or frame segments.

Figure 4:
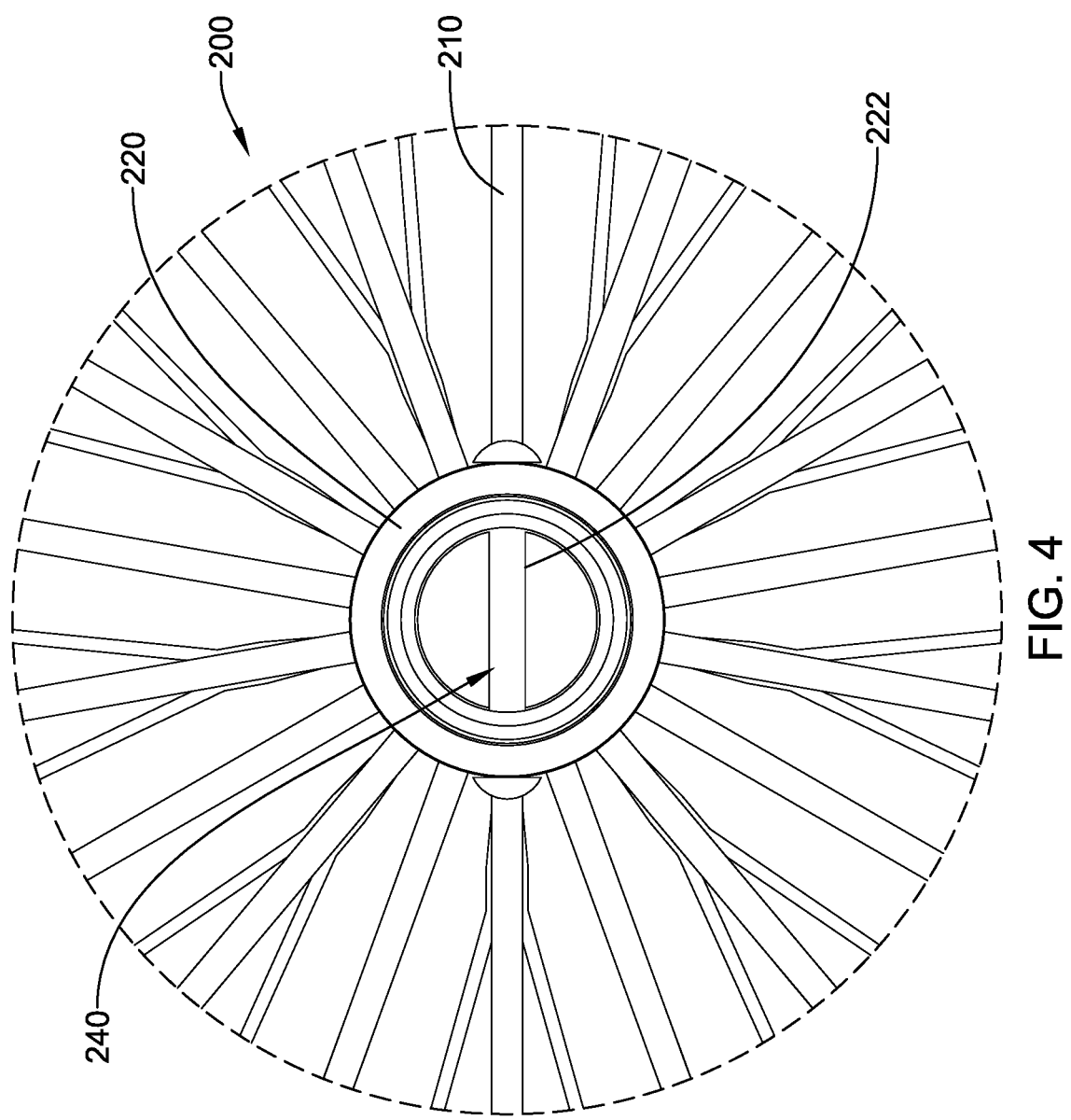
FIGS. 4-5 illustrate detailed top views of selected aspects of the implant for occluding a left atrial appendage.

In some embodiments, the implant 200 and/or the expandable framework 210 may include a proximal hub 220 and/or a distal hub 230. The plurality of interconnected struts and/or frame segments may be fixedly attached to and/or at the proximal hub 220 and/or the distal hub 230. In some embodiments, the expandable framework 210 may include an attachment point 240 configured to secure the expandable framework 210 to the delivery device and/or the tether 140. In some embodiments, the attachment point 240 may be a pin 222 extending laterally across the proximal hub 220, as seen in the top view of FIG. 4 for example. In FIG. 4, the occlusive element 290 has been removed to show other details and/or features.

Figure 5:
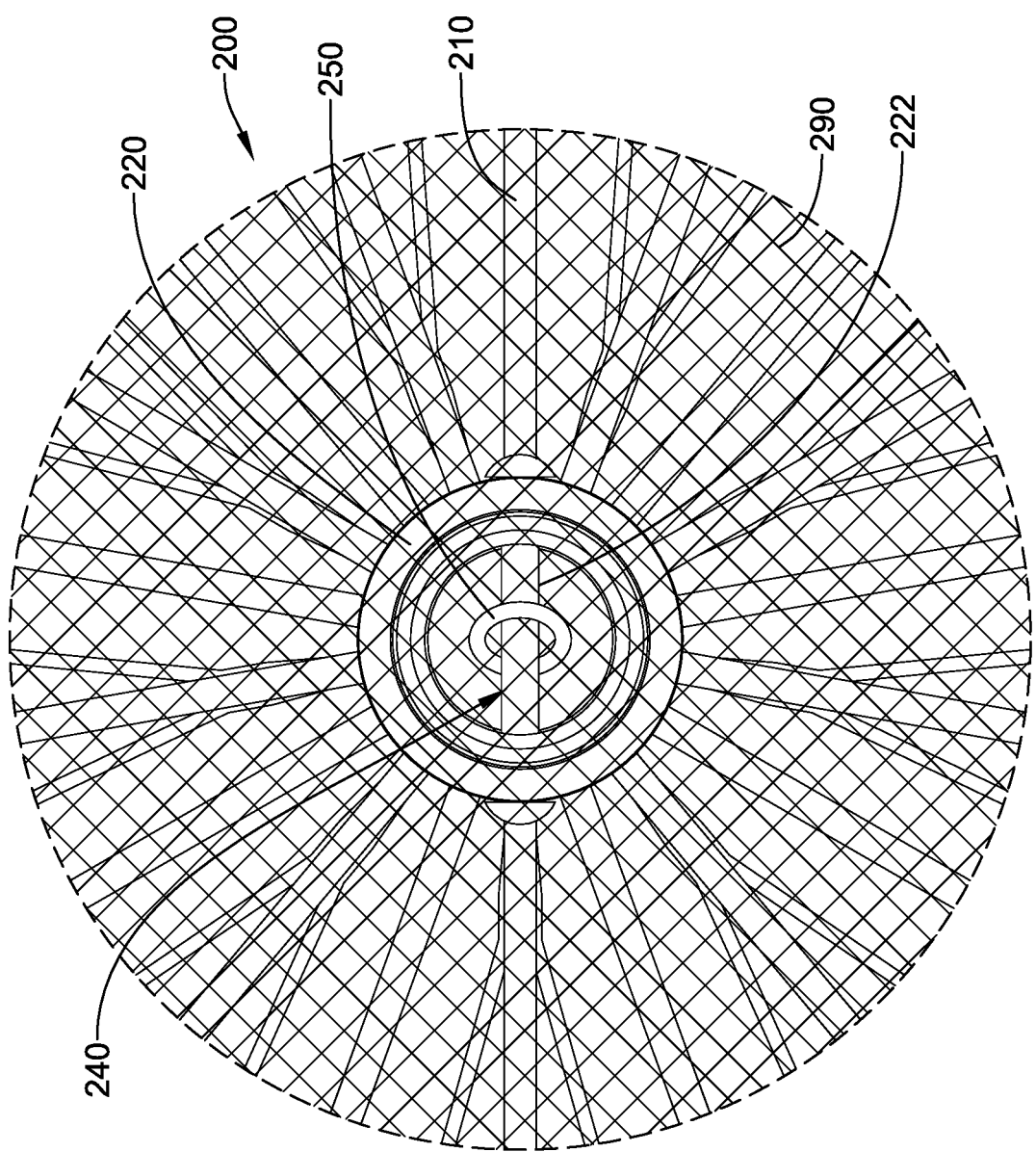

In some embodiments, the implant 200 may include a fastening element 250 securing the occlusive element 290 to the pin 222 and/or the attachment point 240, as seen in the top view of FIG. 5. The occlusive element 290 may extend across and/or may cover the pin 222 and/or the attachment point 240. As also seen in FIG. 5, the occlusive element 290 may include a porous mesh. Some details of the occlusive element 290 are not shown in all figures in the interest of clarity, but it is to be understood that the occlusive element 290 may be and/or may include the porous mesh in some, any, and/or all figures showing the occlusive element 290. In some embodiments, the porous mesh may be a woven structure, a fabric structure, a textile structure, and/or a membrane or film having a plurality of apertures formed therein and/or extending therethrough. In some embodiments, the porous mesh may comprise a plurality of pores, openings, and/or apertures extending through the occlusive element 290 from the first side to the second side. In some embodiments, the plurality of pores, openings, and/or apertures extending through the occlusive element 290 may have a size and/or extent of between about 5 micrometers (microns) and about 500 micrometers, between about 50 micrometers and about 300 micrometers, between about 100 micrometers and about 220 micrometers, between about 140 micrometers and about 180 micrometers, and/or about 160 micrometers. In some embodiments, the plurality of pores, openings, and/or apertures extending through the occlusive element 290 may have a maximum size and/or extent of about 1 millimeter (e.g., 1000 micrometers).

In some embodiments, the occlusive element 290 may include a surface treatment configured to promote endothelization on and/or across the occlusive element 290. In some embodiments, the occlusive element 290 may include the surface treatment disposed on and/or surrounding a portion of an outer surface and/or a proximally-facing surface of the occlusive element 290. In some embodiments, the occlusive element 290 may include the surface treatment disposed on and/or surrounding an entire outer surface and/or an entire proximally-facing surface of the occlusive element 290. In some embodiments, the occlusive element 290 may be elastic and/or stretchable to accommodate changes in shape and/or size of the expandable framework 210 when the expandable framework 210 is shifted toward and/or into the expanded configuration. Some suitable, but non-limiting, examples of materials for the expandable framework 210, the plurality of interconnected struts and/or frame segments, the plurality of anchor members 212, the proximal hub 220, the pin 222, the distal hub 230, the fastening element 250, and/or the occlusive element 290 are discussed below.

As seen in FIG. 5, the fastening element 250 may extend through two or more of the plurality of pores, openings, and/or apertures extending through the occlusive element 290 from the first side to the second side. For example, the fastening element 250 may avoid piercing and/or otherwise compromising the integrity of the occlusive element 290 by passing through existing pores, openings, and/or apertures through the occlusive element 290. The fastening element 250 may extend around the pin 222 and/or the attachment point 240. In some embodiments, the fastening element 250 may wrap around the pin 222 and/or the attachment point 240 multiple times. In some embodiments, the fastening element 250 may be attached to (e.g., tied to, adhered to, bonded to, etc.) the pin 222, the attachment point 240, and/or the occlusive element 290. In some embodiments, the fastening element 250 may be attached to (e.g., tied to, adhered to, bonded to, etc.) itself. For example, the fastening element 250 may be tied in a knot and/or may be bonded to itself to form a single continuous loop and/or structure. In some embodiments, the fastening element 250 may be configured to stabilize the occlusive element 290 relative to the expandable framework 210 and/or the proximal hub 220. For example, the fastening element 250 may reduce and/or prevent axial movement (e.g., "flapping") of the occlusive element 290 relative to the expandable framework 210 and/or the proximal hub 220 caused by normal flow and pressure changes within the left atrium as the heart beats. In some embodiments, the fastening element 250 may be a filament, a thread, a suture, or other suitable flexible elongate element.

Figure 6:
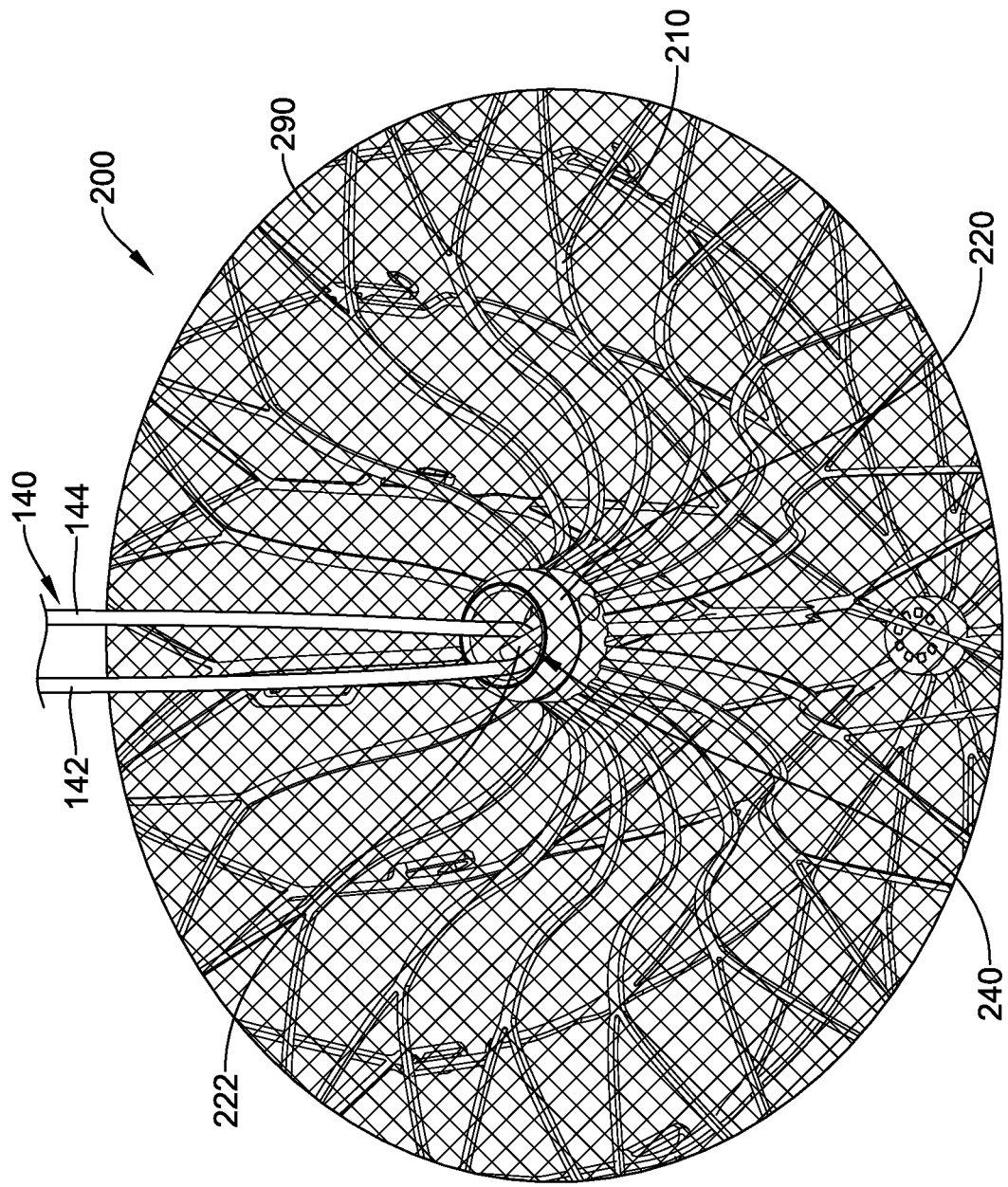
FIG. 6 illustrates a detailed view of selected aspects of the system and implant for occluding a left atrial appendage.

Turning now to FIG. 6, the tether 140 may extend through two or more of the plurality of pores, openings, and/or apertures extending through the occlusive element 290 from the first side of the occlusive element 290 to the second side of the occlusive element 290. For example, the tether 140 may avoid piercing and/or otherwise compromising the integrity of the occlusive element 290 by passing through existing pores, openings, and/or apertures through the occlusive element 290. The tether 140 may extend around the pin 222 and/or the attachment point 240. The first longitudinally extending portion 142 may extend through a first pore, opening, and/or aperture, and/or the second longitudinally extending portion 144 may extend through a second pore, opening, and/or aperture different from the first pore, opening, and/or aperture.

In some embodiments, the tether 140 may extend around the pin 222 and/or the attachment point 240 one time without wrapping and/or completely encircling the pin 222 and/or the attachment point 240. However, it is contemplated that in some embodiments, the tether 140 may wrap around the pin 222 and/or the attachment point 240 multiple times. The first longitudinally extending portion 142 may be disposed on a first side of the pin 222 and/or the attachment point 240, and the second longitudinally extending portion 144 may be disposed on a second side of the pin 222 and/or the attachment point 240. While not explicitly illustrated in FIG. 6, the fastening element 250 may be used and/or present in conjunction with the tether 140 and should be understood as being a part of the structure shown in FIG. 6.

Figure 7:
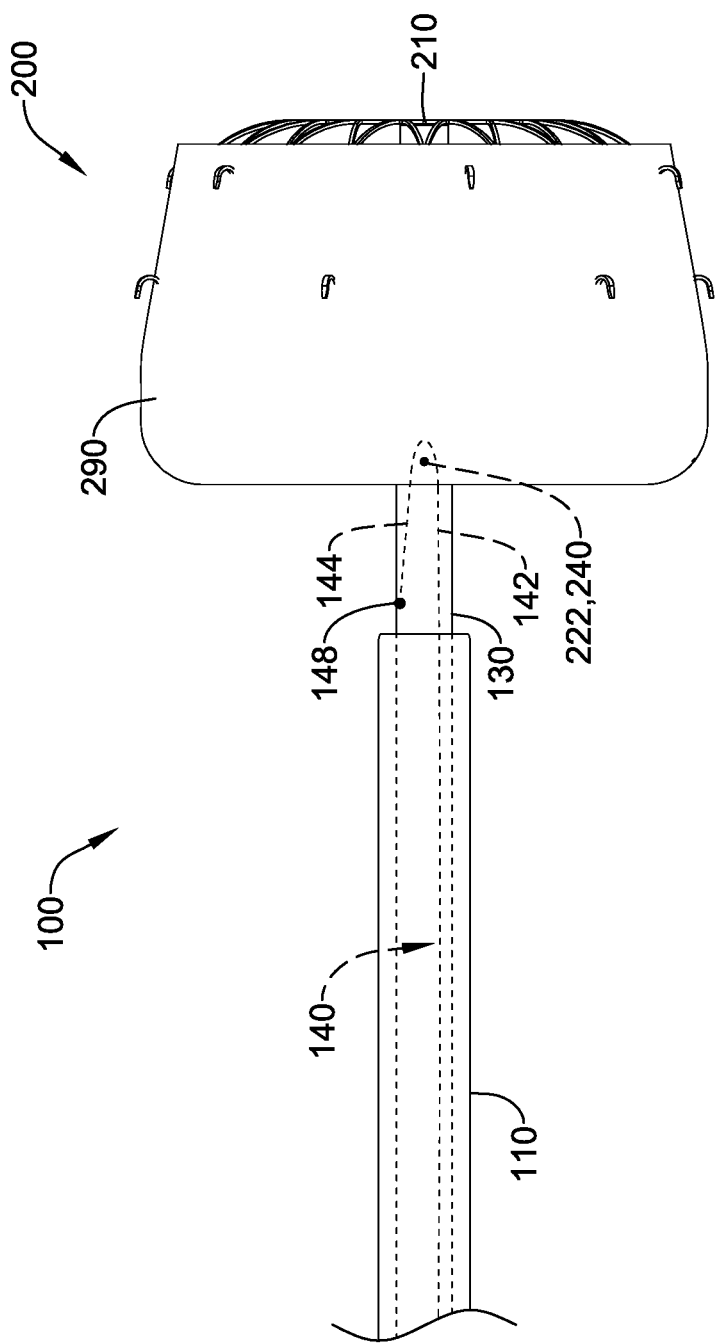
FIG. 7 illustrates selected aspects of the system and implant for occluding a left atrial appendage.

The tether 140 may be used to secure the implant 200 to the delivery device. Tension applied to the tether 140 relative to the inner elongate member 130 may pull the implant 200 and/or the expandable framework 210 into engagement with and/or against a distal end of the inner elongate member 130, as seen in FIG. 7. The occlusive element 290 may be squeezed and/or pinched between the expandable framework 210 and the distal end of the inner elongate member 130. The tether 140 may be used in positioning, repositioning, and/or retrieval of the implant 200.

Figure 8:
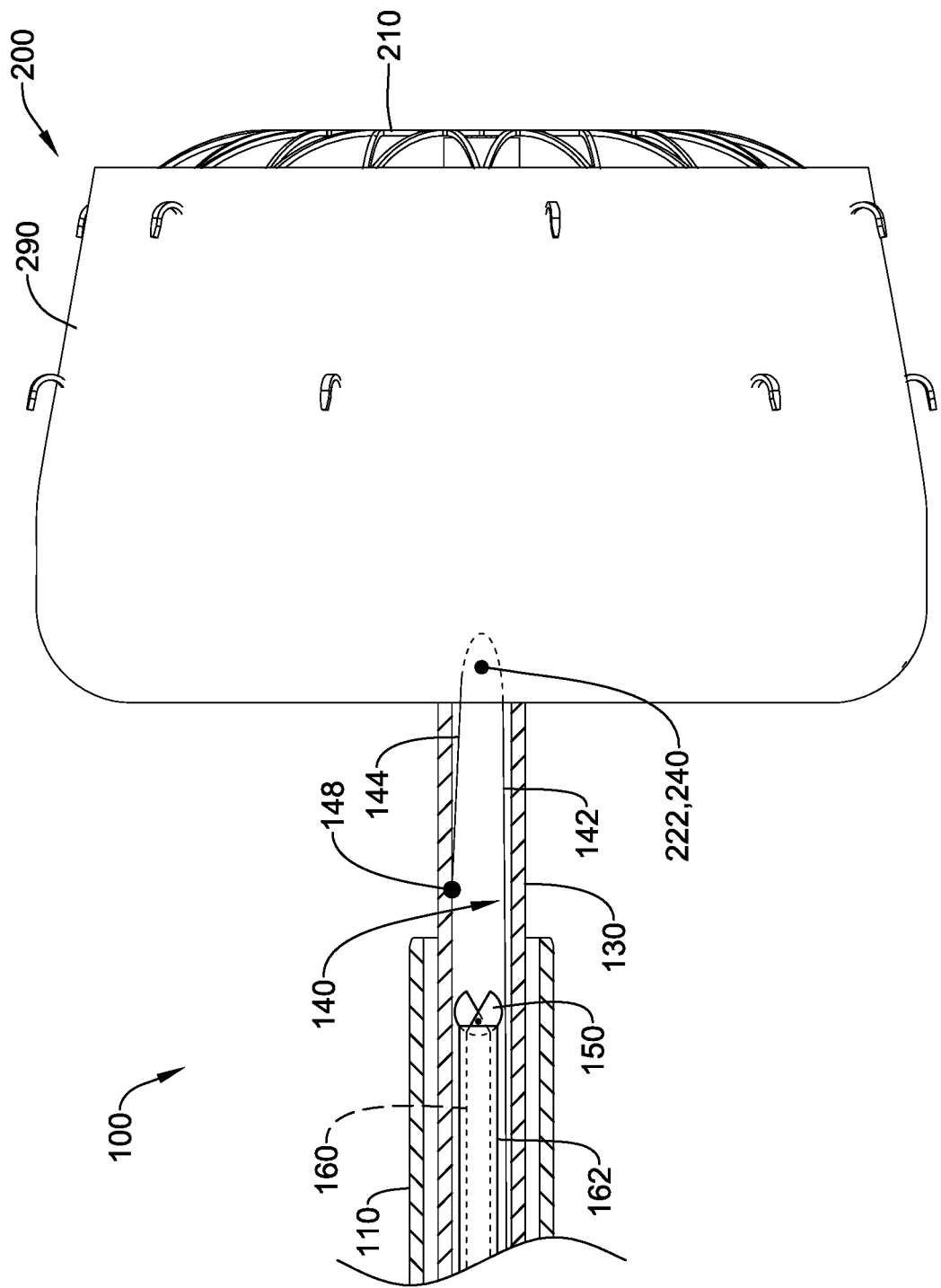
FIGS. 8-11 illustrate selected aspects of releasing the implant from the system for occluding a left atrial appendage.

FIGS. 7 and 8 illustrate additional aspects of the system 100. As may be seen in the figures, the tether 140 may extend longitudinally within the lumen (or within at least one of the plurality of lumens) of the inner elongate member 130. The tether 140 may engage the pin 222 and/or the attachment point 240 in a delivery configuration of the system 100, as shown in FIGS. 6 and 7 for example. The tether 140 may extend through the occlusive element 290, as described herein, in the delivery configuration of the system 100.

In some embodiments, the second longitudinally extending portion 144 of the tether 140 may be secured and/or fixedly attached to the inner elongate member 130 at a tether attachment point 148 proximate a distal end of the inner elongate member 130, such as by adhesive bonding, mechanical attachment, or other suitable means. In some embodiments, a distal end of the tether 140 may be secured and/or fixedly attached to the inner elongate member 130 at the tether attachment point 148 proximate the distal end of the inner elongate member 130. Applying tension to the first longitudinally extending portion 142 of the tether 140 may pull the implant 200 and/or the expandable framework 210 into engagement with and/or against the distal end of the inner elongate member 130.

The system 100 may further include a release mechanism disposed within the delivery device, the lumen of the outer sheath 110, and/or the lumen of the inner elongate member 130. For the purpose of illustration, the release mechanism is shown in FIG. 8 within the lumen of the inner elongate member 130, but this is not intended to be limiting, as the release mechanism may be disposed within the lumen of the outer sheath 110 and/or may be disposed alongside (and outside of) the inner elongate member 130. The release mechanism may be configured to sever the tether 140 within the lumen of the inner elongate member 130 and/or the outer sheath 110.

In some embodiments, the release mechanism may include a cutting blade 150 disposed within the delivery device, the inner elongate member 130, and/or the outer sheath 110. In the configuration shown in FIG. 8, the release mechanism may be movably and/or slidably disposed within the delivery device, the inner elongate member 130, and/or the outer sheath 110. The release mechanism may include an elongate shaft 160 movably and/or slidably disposed within an elongate tube 162. The elongate tube 162 may be slidably disposed within the delivery device, the inner elongate member 130, and/or the outer sheath 110. The cutting blade 150 may be pivotably attached at a distal end of the elongate shaft 160, such that axial translation of the elongate shaft 160 relative to the elongate tube 162 may actuate the cutting blade 150. For example, distal relative movement of the elongate tube 162 over the elongate shaft 160 may force a distal end of the elongate tube 162 into contact with the cutting blade 150, thereby pivoting and/or actuating the cutting blade 150 as the elongate tube 162 is advanced over the cutting blade 150. Similarly, proximal retraction of the elongate shaft 160 relative to the elongate tube 162 may force the distal end of the elongate tube 162 into contact with the cutting blade 150, thereby pivoting and/or actuating the cutting blade 150 as the elongate shaft 160 and/or the cutting blade 150 is retracted within the elongate tube 162. When the user is ready to release the implant 200, the cutting blade 150 may be engaged with the tether 140 near, adjacent to, and/or proximate the tether attachment point 148, the distal end of the inner elongate member 130, and/or the distal end of the outer sheath 110, and the release mechanism may be actuated to sever the tether 140.

Figure 9:
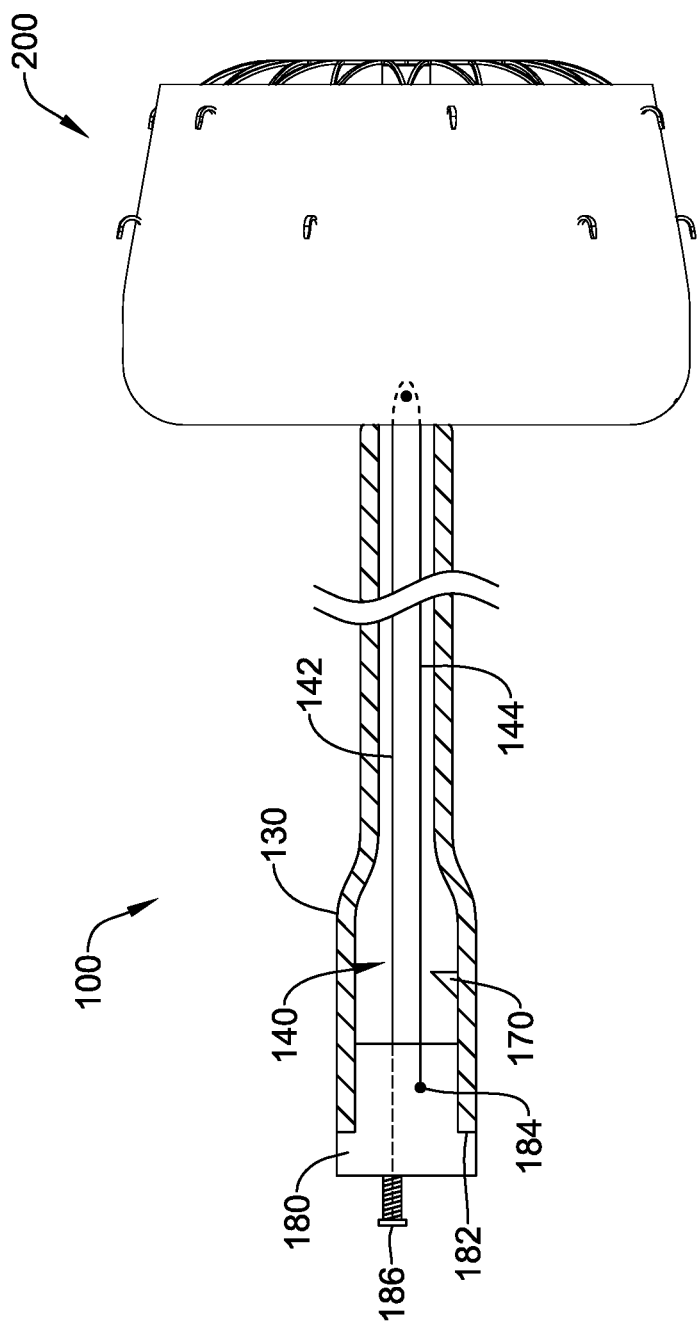
Figure 10:
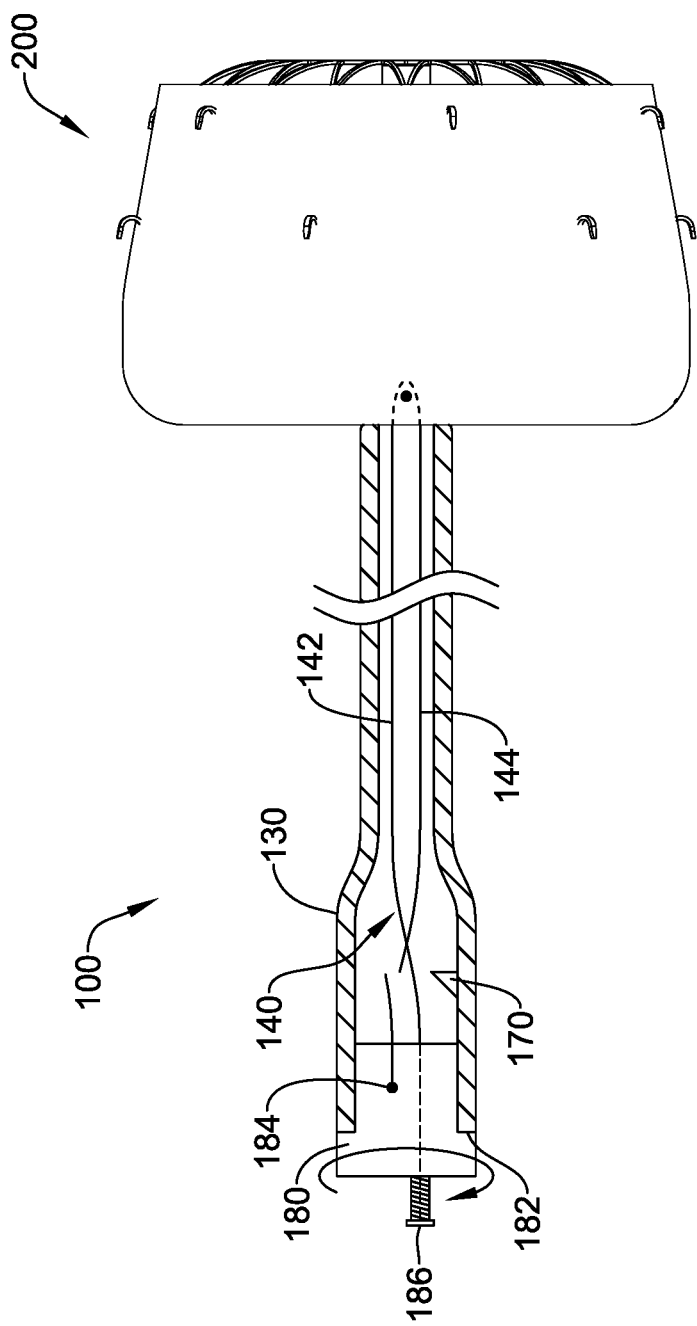
Figure 11:
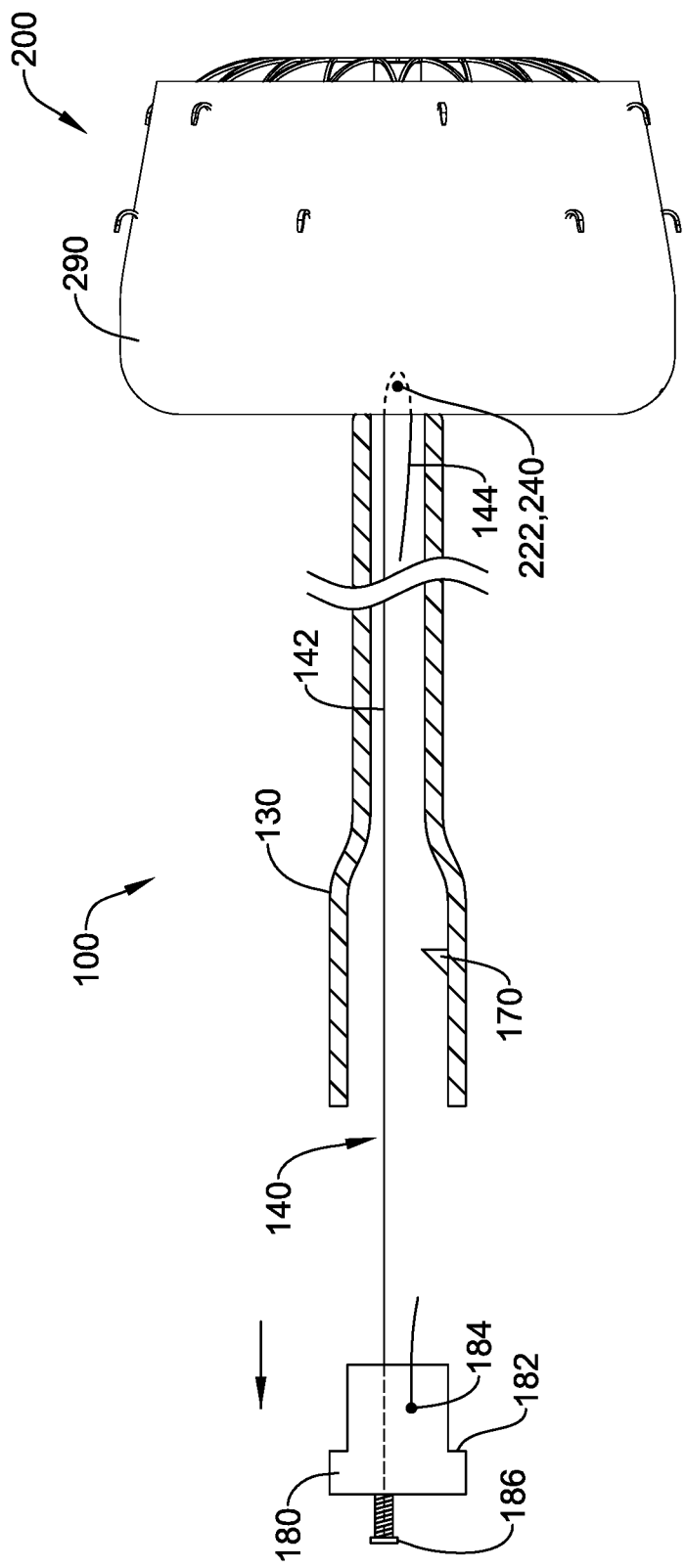

In another configuration, the release mechanism may include a cutting blade 170 disposed within the delivery device, the inner elongate member 130, and/or the outer sheath 110. In the configuration shown in FIGS. 9-11, the cutting blade 170 may be fixedly attached to an inner surface of the inner elongate member 130 and/or the outer sheath 110. For simplicity, only the inner elongate member 130 is illustrated in FIGS. 9-11, but it should be understood that the outer sheath 110 could be used in place of the inner elongate member 130 illustrated and/or that the outer sheath 110 may be also present as described herein. In some embodiments, the cutting blade 170 may extend through a side wall of the inner elongate member 130 and/or the outer sheath 110. In some embodiments, the cutting blade 170 may be retractable and/or movable with respect to the side wall of the inner elongate member 130 and/or the outer sheath 110. For example, the cutting blade 170 may be extended and/or inserted laterally through the side wall of the inner elongate member 130 and/or the outer sheath 110 by the user when the user is ready to sever the tether 140. In some embodiments, the cutting blade 170 may be disposed near, adjacent to, and/or proximate a proximal end of the inner elongate member 130 and/or the outer sheath 110. In some embodiments, the system 100 and/or the release mechanism may further comprise a turnstile 180 movably engaged with the proximal end of the inner elongate member 130 and/or the outer sheath 110. The turnstile 180 may be rotatable and/or axially translatable relative to the proximal end of the delivery device, the inner elongate member 130, and/or the outer sheath 110. A distally-facing shoulder 182 of the turnstile 180 may engage with the proximal end of the delivery device, the inner elongate member 130, and/or the outer sheath 110. The distally-facing shoulder 182 may limit and/or prevent distal translation of the turnstile 180 relative to the proximal end of the delivery device, the inner elongate member 130, and/or the outer sheath 110 in the delivery configuration, while permitting proximal translation of the turnstile 180 relative to the proximal end of the delivery device, the inner elongate member 130, and/or the outer sheath 110 in the delivery configuration.

Figure 12:
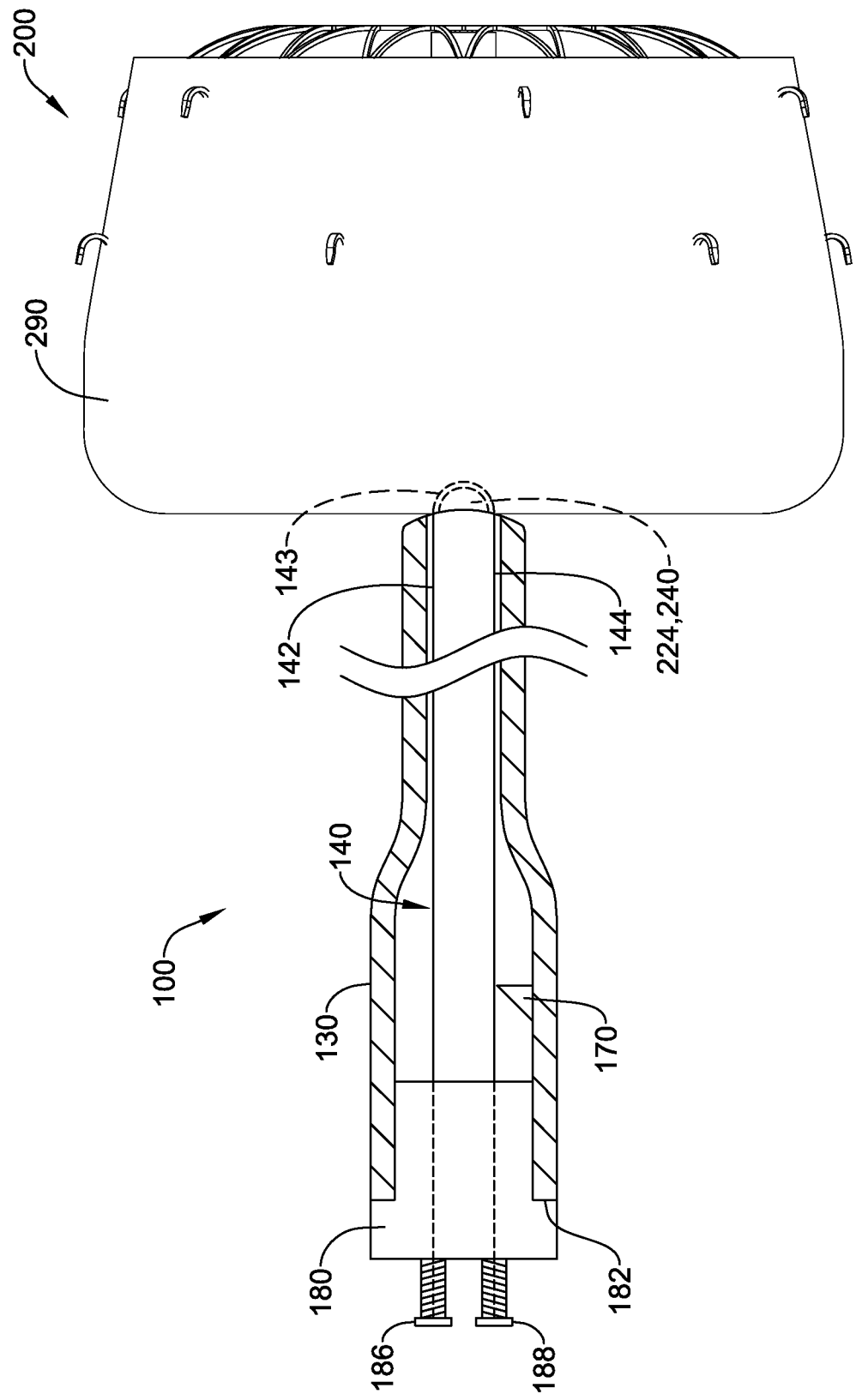
FIGS. 12-15 illustrate selected aspects of the system and implant for occluding a left atrial appendage.

The tether 140 may extend through the lumen of the inner elongate member 130 and/or the outer sheath 110. The second longitudinally extending portion 144 may be fixedly attached to the turnstile 180 at a tether attachment point 184. The first longitudinally extending portion 142 may extend through the turnstile 180 to engage with a first adjustment element 186. The first adjustment element 186 may be configured to translate axially relative to the turnstile 180 to adjust tension applied to the tether 140. In some embodiments, the first adjustment element 186 may include a threaded member, a spring member, a slide member, a cam member, or other suitable means of applying tension to the tether 140, such as via axial translation. In some embodiments, the second longitudinally extending portion 144 may extend through the turnstile 180 to engage with a second adjustment element 188 (e.g., FIG. 12), which may be of similar form and/or construction as the first adjustment element 186. Adjustment of only one of the first adjustment element 186 and the second adjustment element 188 is necessary to change the tension applied to the tether 140, but either one (or both) of the first adjustment element 186 and/or the second adjustment element 188 may be adjusted to apply tension to the tether 140 as needed or desired.

When the user is ready to release the implant 200, the turnstile 180 may be rotated relative to a proximal end of the delivery device, the inner elongate member 130, and/or the outer sheath 110 to engage the tether 140 with the cutting blade 170, thereby severing the tether 140, as shown in FIG. 10. In some embodiments, extending and/or inserting the cutting blade 170 through the side wall of the inner elongate member 130 and/or the outer sheath 110 may partially sever the tether 140, but rotation of the turnstile 180 may still be necessary to ensure that the tether 140 is severed completely. After severing the tether 140, the turnstile 180 may be translated proximally relative to the proximal end of the delivery device, the inner elongate member 130, and/or the outer sheath 110, thereby pulling the tether 140 around the pin 222 and/or the attachment point 240 and through the occlusive element 290 to disengage the tether 140 from the pin 222 and/or the attachment point 240, as shown in FIG. 11. The tether 140 may be disengaged from the pin 222 and/or the attachment point 240 in a released configuration of the system 100.

In some embodiments, the system 100 may include a feature or features that permit the implant 200 to be angled relative to a central longitudinal axis of the delivery device, the inner elongate member 130, and/or the outer sheath 110, as seen in FIGS. 12-15. In some embodiments, the inner elongate member 130 may include a distal end that is curved, convex, and/or rounded. In some embodiments, the attachment point 240 may include a cam member 224 extending laterally across the proximal hub 220 of the expandable framework 210. The cam member 224 may include a convex distal side, and a concave proximal side configured to cooperate with the distal end of the inner elongate member 130. The occlusive element 290 may extend across and/or cover the proximal hub 220 and/or the cam member 224, such that the proximal hub 220 and/or the cam member 224 is entirely disposed on the second (e.g., the distal) side of the occlusive element 290.

The tether 140 may engage the cam member 224 and/or the attachment point 240 in the delivery configuration of the system 100, as shown in FIG. 12-15 for example. The tether 140 may extend through the occlusive element 290, as described herein, in the delivery configuration of the system 100. The tether 140 may extend through two or more of the plurality of pores, openings, and/or apertures extending through the occlusive element 290 from the first side of the occlusive element 290 to the second side of the occlusive element 290. For example, the tether 140 may avoid piercing and/or otherwise compromising the integrity of the occlusive element 290 by passing through existing pores, openings, and/or apertures through the occlusive element 290. The tether 140 may extend around the cam member 224 and/or the attachment point 240. The first longitudinally extending portion 142 may extend through a first pore, opening, and/or aperture, and/or the second longitudinally extending portion 144 may extend through a second pore, opening, and/or aperture different from the first pore, opening, and/or aperture. A cam member engaging portion 143 of the tether 140 may extend around the cam member 224 and/or the attachment point 240 between the first longitudinally extending portion 142 and the second longitudinally extending portion 144.

Figure 13:
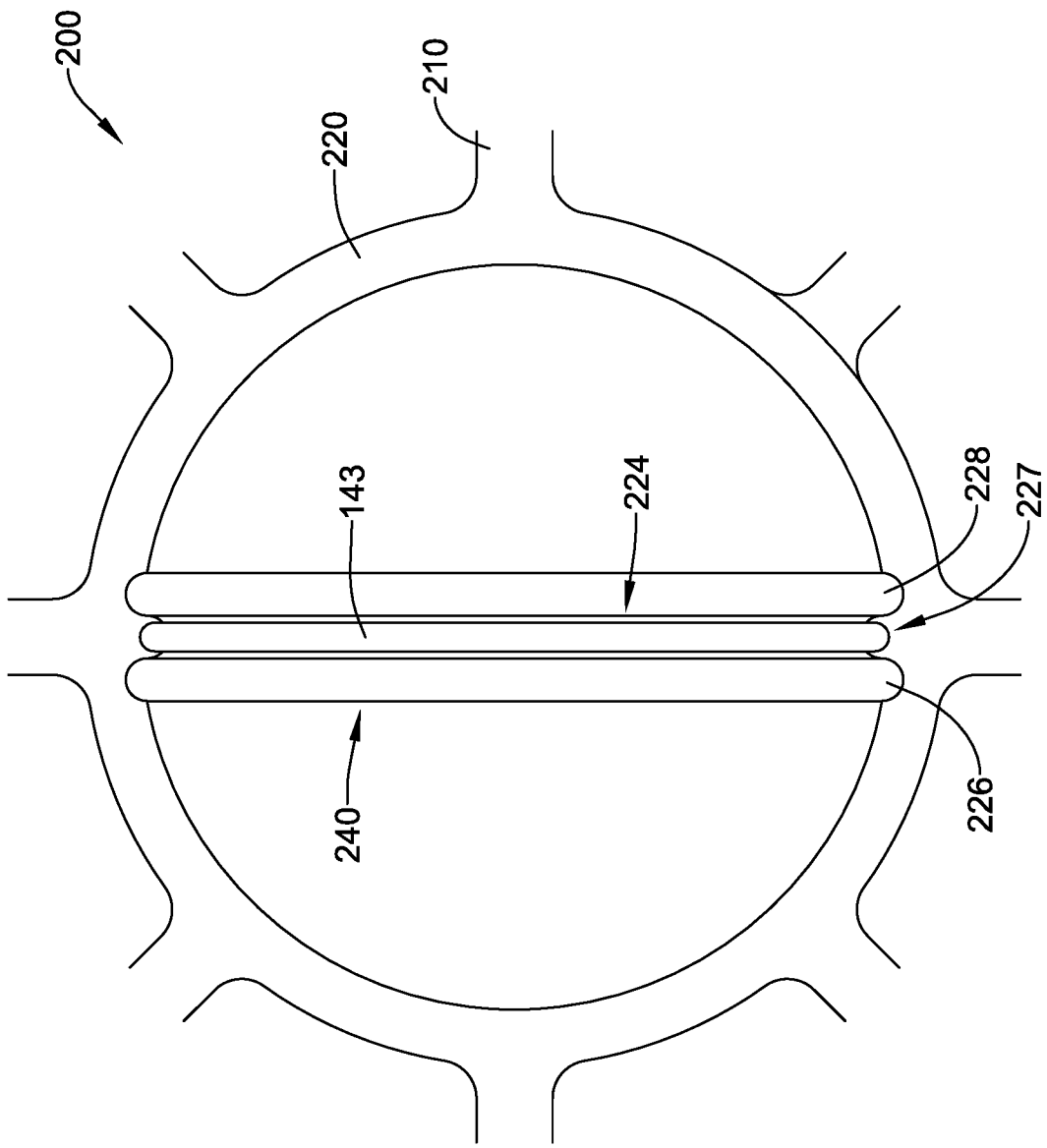

FIG. 13 illustrates the cam member 224 as seen from the bottom or back side view of the proximal hub 220. The cam member 224 extends laterally across the proximal hub 220 of the expandable framework 210. The cam member 224 may be fixedly attached to the proximal hub 220. The convex distal side of the cam member 224 may include a first lateral shoulder 226 and a second lateral shoulder 228. The first lateral shoulder 226 and the second lateral shoulder 228 may form a channel 227 extending laterally across the proximal hub 220 between the first lateral shoulder 226 and the second lateral shoulder 228. The channel 227 may be configured to receive and/or engage the cam member engaging portion 143 of the tether 140. The cam member engaging portion 143 may be disposed between the first longitudinally extending portion 142 and the second longitudinally extending portion 144. The tether 140 may pass through openings disposed between the cam member 224 and the proximal hub 220 at both opposing lateral ends and/or sides of the cam member 224.

In some embodiments, the cam member engaging portion 143 of the tether 140 may extend around the convex distal side of the cam member 224 and/or the attachment point 240 one time without wrapping and/or completely encircling the cam member 224 and/or the attachment point 240. However, it is contemplated that in some embodiments, the cam member engaging portion 143 of the tether 140 may wrap around the cam member 224 and/or the attachment point 240 multiple times. The first longitudinally extending portion 142 may be disposed on a first lateral side of the cam member 224 and/or the attachment point 240, and the second longitudinally extending portion 144 may be disposed on a second lateral side of the cam member 224 and/or the attachment point 240. Both the first longitudinally extending portion 142 and the second longitudinally extending portion 144 may extend proximally away from the cam member 224 and/or the attachment point 240.

The tether 140 may be used to secure the implant 200 to the delivery device. Turning back to FIG. 12, tension applied equally to the first longitudinally extending portion 142 and the second longitudinally extending portion 144 of the tether 140 relative to the inner elongate member 130 may pull the implant 200, the expandable framework 210, the proximal hub 220, and/or the concave proximal side of the cam member 224 into engagement with and/or against the distal end of the inner elongate member 130. When tension is applied to the tether 140, the occlusive element 290 may be squeezed and/or pinched between the distal end of the inner elongate member 130 and the proximal hub 220 and/or the concave proximal side of the cam member 224.

Figure 14:
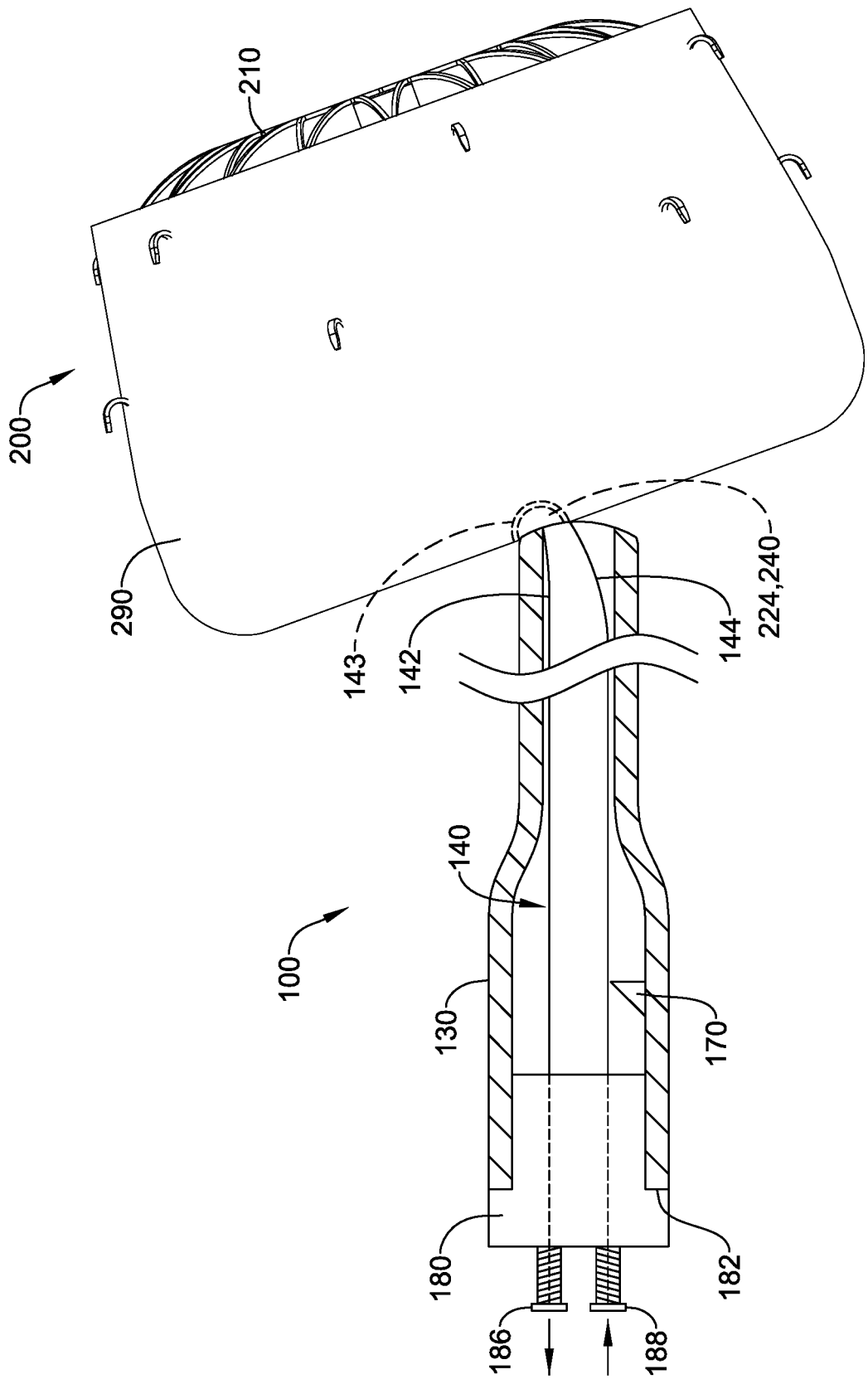

In some embodiments, the concave proximal side of the cam member 224 may function as a rocker and/or slider feature that cooperates with the distal end of the inner elongate member 130. Tension applied to and/or axial translation in a proximal direction of the first longitudinally extending portion 142 using the first adjustment element 186 (and/or slack from loosening tension applied to and/or axial translation in a distal direction of the second longitudinally extending portion 144 using the second adjustment element 188) may shift the cam member 224, the expandable framework 210, and/or the implant 200 laterally relative to the central longitudinal axis of the delivery device, the inner elongate member 130, and/or the outer sheath 110. As such, tension applied to and/or axial translation in the proximal direction of the first longitudinally extending portion 142 using the first adjustment element 186 (and/or slack from loosening tension applied to and/or axial translation in the distal direction of the second longitudinally extending portion 144 using the second adjustment element 188 may be configured to angle the expandable framework 210 relative to the central longitudinal axis of the delivery device, the inner elongate member 130, and/or the outer sheath 110, as seen in FIG. 14. In some embodiments, the expandable framework 210 may be angled and/or oriented at an oblique angle relative to central longitudinal axis of the delivery device, the inner elongate member 130, and/or the outer sheath 110.

Similarly, tension applied to and/or axial translation in a proximal direction of the to second longitudinally extending portion 144 using the second adjustment element 188 (and/or slack from loosening tension applied to and/or axial translation in a distal direction of the first longitudinally extending portion 142 using the first adjustment element 186) may shift the cam member 224, the expandable framework 210, and/or the implant 200 laterally relative to the central longitudinal axis of the delivery device, the inner elongate member 130, and/or the outer sheath 110. As such, tension applied to and/or axial translation in the proximal direction of the second longitudinally extending portion 144 using the second adjustment element 188 (and/or slack from loosening tension applied to and/or axial translation in the distal direction of the first longitudinally extending portion 142 using the first adjustment element 186) may be configured to angle the expandable framework 210 relative to the central longitudinal axis of the delivery device, the inner elongate member 130, and/or the outer sheath 110, as seen in FIG. 15. In some embodiments, the expandable framework 210 may be angled and/or oriented at an oblique angle relative to central longitudinal axis of the delivery device, the inner elongate member 130, and/or the outer sheath 110.

Figure 18:
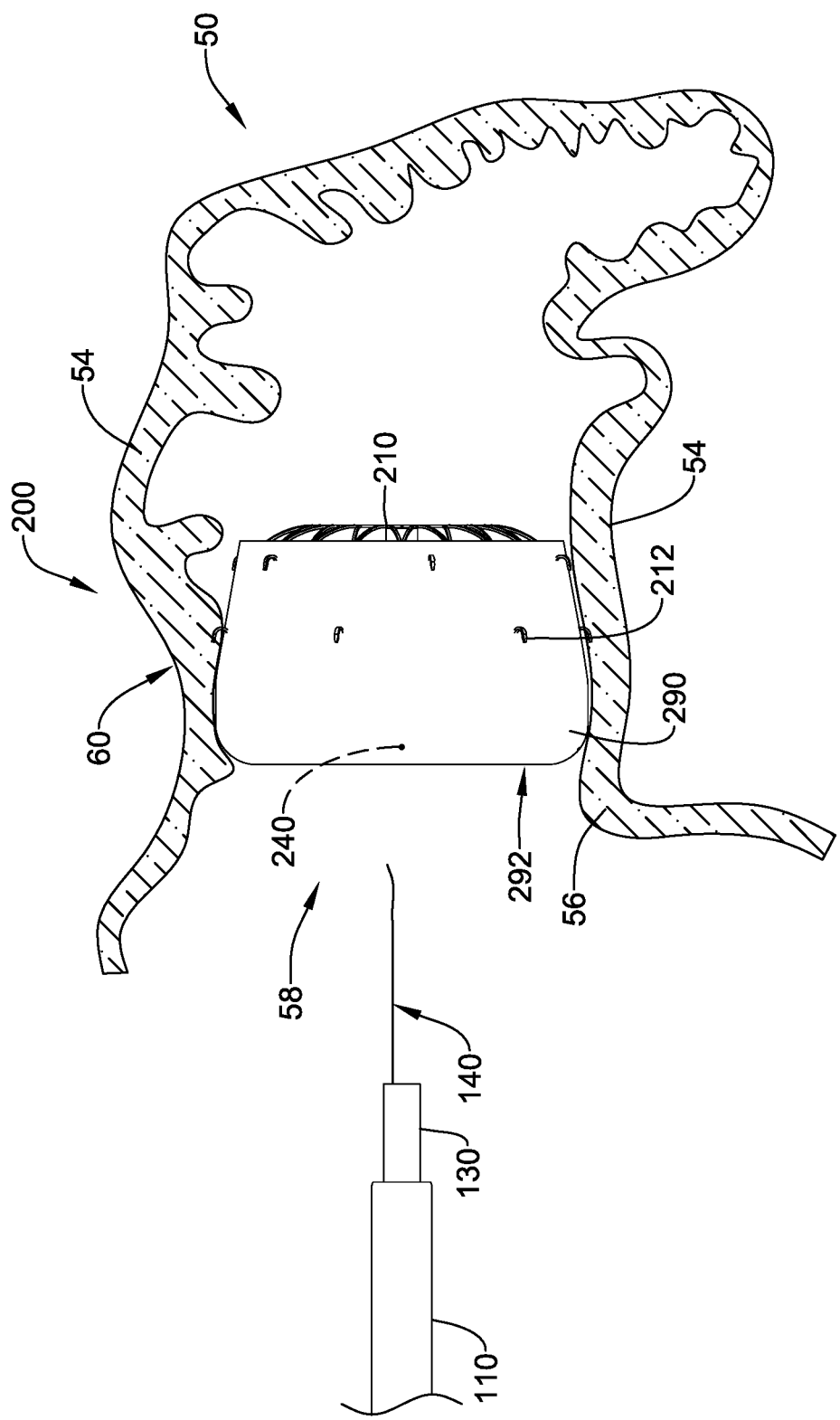

FIGS. 16-18 illustrate an example left atrial appendage 50, which may be attached to and in fluid communication with a left atrium of a heart (not shown), in partial cross-section. The left atrial appendage 50 may have a complex geometry and/or irregular surface area. Those skilled in the art will recognize that the illustrated left atrial appendage is merely one of many possible shapes and sizes for the left atrial appendage, which may vary from patient to patient. Those of skill in the art will also recognize that the medical devices and methods disclosed herein may be adapted for various sizes and shapes of the left atrial appendage, as necessary. The left atrial appendage 50 may include a generally longitudinal axis arranged along a depth of a main body 60 of the left atrial appendage 50. The main body 60 may include a wall 54 and an ostium 56 forming a proximal mouth 58 in communication with the left atrium of the heart. In some embodiments, a lateral extent of the ostium 56 and/or the wall 54 may be smaller or less than a depth of the main body 60 along the longitudinal axis, or a depth of the main body 60 may be greater than a lateral extent of the ostium 56 and/or the wall 54. In some embodiments, the left atrial appendage 50 may include a tail-like element associated with a distal portion of the main body 60 relative to the ostium 56, which element may protrude radially or laterally away from the main body 60.

A method of occluding the left atrial appendage 50 may comprise advancing the implant 200 configured to occlude the left atrial appendage 50 in the delivery configuration, within a lumen of the delivery device and/or the outer sheath 110 with the expandable framework 210 in the collapsed configuration (e.g., FIG. 1), into the left atrial appendage 50. In some embodiments, the implant 200 may be advanced into the left atrial appendage 50 within and/or using the system 100. In some embodiments, the implant 200 may be advanced percutaneously within the patient's vasculature to the left atrial appendage 50. In some embodiments, the implant 200 may be advanced using a different access method including, but not limited to, transapical access, transseptal access, or other surgical access.

The method may include deploying the implant 200 within the left atrial appendage 50, as seen in FIG. 16 for example. Deploying the implant 200 may include expanding and/or shifting the expandable framework 210 into the expanded configuration. In some embodiments, deploying the implant 200 may include axially translating the outer sheath 110 relative to the inner elongate member 130 to expose the implant 200. The inner elongate member 130 may be engaged with the expandable framework 210 and/or the proximal hub 220 during delivery and/or deployment of the implant 200. In the expanded configuration, the plurality of anchor members 212 may engage with the wall 54 of the left atrial appendage 50.

The method may include releasing the implant 200 within the left atrial appendage 50. In some embodiments, releasing the implant 200 may include severing the tether 140 securing the implant 200 to the delivery device. FIG. 17 illustrates the tether 140 after the severing the tether 140 using the release mechanism of the system 100. In some embodiments, rotation of the turnstile 180 (e.g., FIG. 10) relative to the proximal end of the delivery device, the inner elongate member 130, and/or the outer sheath 110 severs the tether 140, as discussed herein. In some embodiments, axial translation of the tether 140 prior to severing the tether 140 angles the expandable framework 210 relative to a central longitudinal axis of the delivery device, the inner elongate member 130, and/or the outer sheath 110. Similarly, in some embodiments, axial translation of the tether 140 prior to severing the tether 140 may angle the expandable framework 210 relative to the generally longitudinal axis of the left atrial appendage 50.

In some embodiments, the implant 200 and/or the expandable framework 210 may be oriented at an oblique angle to the generally longitudinal axis of the left atrial appendage 50. Engagement of the distal end of the inner elongate member 130 with the cam member 224 may permit and/or facilitate off-axis orientation of the implant 200 and/or the expandable framework 210 relative to the generally longitudinal axis of the left atrial appendage 50, which may ease positioning, implantation, and/or sealing within an irregularly-shaped and/or oriented left atrial appendage 50.

After releasing the implant 200, all metallic materials of the implant 200 may be disposed distal of a proximal-facing surface 292 of the occlusive element 290, such that all metallic materials are effectively removed from the blood stream and/or are no longer exposed to moving fluid and/or blood within the circulatory system (including the left atrium of the heart) of the patient. In some embodiments, after releasing the implant 200, all other structure of the implant 200 and/or the expandable framework 210 may be disposed distal of the proximal-facing surface 292 of the occlusive element 290, such that only the proximal-facing surface 292 of the occlusive element 290 remains exposed to and/or in intimate contact with the blood stream and/or moving fluid and/or blood within the circulatory system (including the left atrium of the heart) of the patient. For example, the expandable framework 210, the proximal hub 220, the distal hub 230, the attachment point 240, the plurality of anchor members 212, etc. may be disposed distal of the proximal-facing surface 292 of the occlusive element 290.

After release of the implant 200, subsequent proximal retraction of the turnstile 180 relative to the proximal end of the delivery device (e.g., FIG. 11), the inner elongate member 130, and/or the outer sheath 110 may disengage the tether 140 from the implant 200, the expandable framework 210, and/or the attachment point 240, as seen in FIG. 18. In some embodiments, proximal retraction of the turnstile 180 relative to the proximal end of the delivery device (e.g., FIG. 11), the inner elongate member 130, and/or the outer sheath 110 may pull the tether 140 through the plurality of pores, openings, and/or apertures extending through the occlusive element 290. The tether 140 may be disengaged from the attachment point 240, the pin 222, and/or the cam member 224 in the released configuration.

Figure 19:
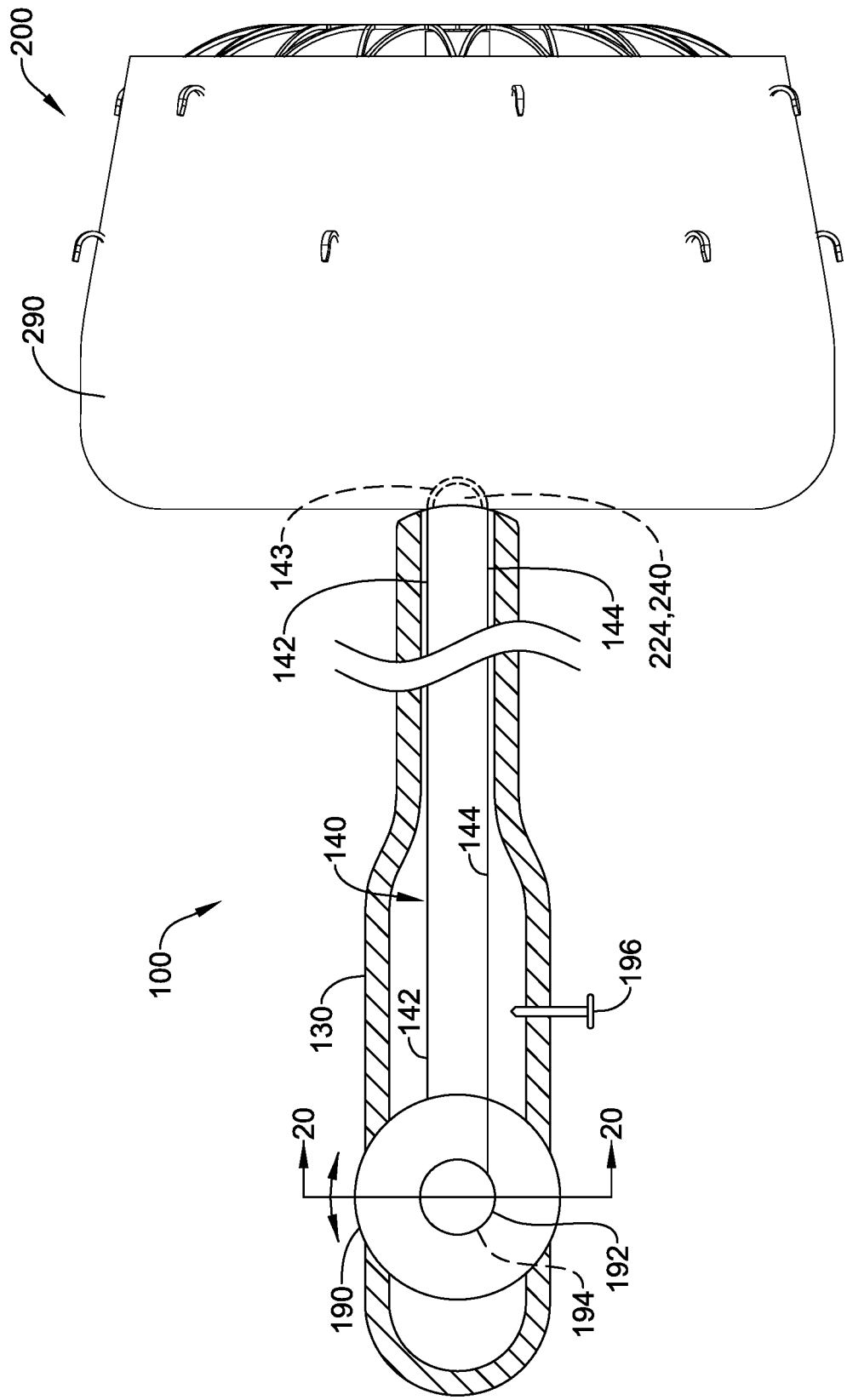
FIGS. 19-20 illustrate selected alternative aspects of the system and implant for occluding a left atrial appendage.
Figure 20:
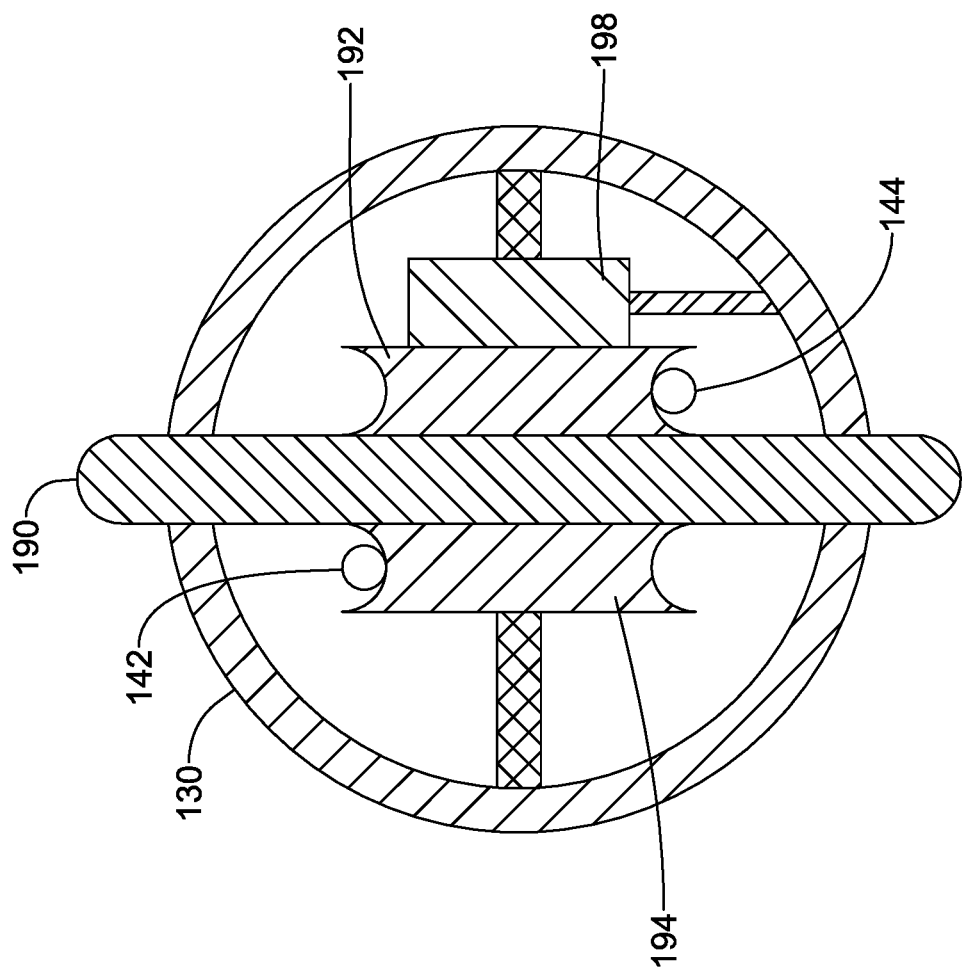

In some embodiments, the system 100 may include a feature or features that permit the implant 200 to be angled relative to the central longitudinal axis of the delivery device, the inner elongate member 130, and/or the outer sheath 110, as seen in FIGS. 19-20. In some embodiments, the inner elongate member 130 may include a distal end that is curved, convex, and/or rounded. In some embodiments, the attachment point 240 may include a cam member 224 extending laterally across the proximal hub 220 of the expandable framework 210. The cam member 224 may include a convex distal side, and a concave proximal side configured to cooperate with the distal end of the inner elongate member 130. The occlusive element 290 may extend across and/or cover the proximal hub 220 and/or the cam member 224, such that the proximal hub 220 and/or the cam member 224 is entirely disposed on the second (e.g., the distal) side of the occlusive element 290.

The tether 140 may engage the cam member 224 and/or the attachment point 240 in the delivery configuration of the system 100. The tether 140 may extend through the occlusive element 290, as described herein, in the delivery configuration of the system 100. The tether 140 may extend through two or more of the plurality of pores, openings, and/or apertures extending through the occlusive element 290 from the first side of the occlusive element 290 to the second side of the occlusive element 290. For example, the tether 140 may avoid piercing and/or otherwise compromising the integrity of the occlusive element 290 by passing through existing pores, openings, and/or apertures through the occlusive element 290. The tether 140 may extend around the cam member 224 and/or the attachment point 240. The first longitudinally extending portion 142 may extend through a first pore, opening, and/or aperture, and/or the second longitudinally extending portion 144 may extend through a second pore, opening, and/or aperture different from the first pore, opening, and/or aperture. A cam member engaging portion 143 of the tether 140 may extend around the cam member 224 and/or the attachment point 240 between the first longitudinally extending portion 142 and the second longitudinally extending portion 144.

In some embodiments, the inner elongate member 130 may include a rotatable wheel 190 protruding from the inner elongate member 130 such that the rotatable wheel 190 may be rotated clockwise and/or counterclockwise (as viewed from the side of the system 100 and/or the inner elongate member 130), as seen in FIG. 19. The first longitudinally extending portion 142 of the tether 140 may be fixedly attached to and/or configured to wrap around a first spool 194 fixedly attached to a first side of the rotatable wheel 190. The second longitudinally extending portion 144 of the tether 140 may be fixedly attached to and/or configured to wrap around a second spool 192 fixedly attached to a second side of the rotatable wheel 190 opposite the first side. The first longitudinally extending portion 142 and the second longitudinally extending portion 144 may be configured to wrap around the first spool 194 and the second spool 192, respectively, in opposite directions. For example, the first longitudinally extending portion 142 may wrap around the first spool 192 in a clockwise direction and the second longitudinally extending portion 144 may wrap around the second spool 194 in a counterclockwise direction, or vice versa. In some embodiments, the rotatable wheel 190 may include a detent clicker 198 or similar structure configured to engage with a stopping element extending from and/or fixedly attached to the inner elongate member 130, as seen in FIG. 20, to thereby maintain the rotatable wheel in a fixed rotational position when the rotatable wheel 190 is not being rotated by a user.

In some embodiments, the concave proximal side of the cam member 224 may function as a rocker and/or slider feature that cooperates with the distal end of the inner elongate member 130. Tension applied to and/or axial translation in a proximal direction of the first longitudinally extending portion 142 and/or tension applied to and/or axial translation in a distal direction of the second longitudinally extending portion 144, or vice versa, using the rotatable wheel 190 may shift the cam member 224, the expandable framework 210, and/or the implant 200 laterally relative to the central longitudinal axis of the delivery device, the inner elongate member 130, and/or the outer sheath 110, similar to other configurations described herein. As such, applied to and/or axial translation in a proximal direction of the first longitudinally extending portion 142 and/or tension applied to and/or axial translation in a distal direction of the second longitudinally extending portion 144, or vice versa, using the rotatable wheel 190 may be configured to angle the expandable framework 210 relative to the central longitudinal axis of the delivery device, the inner elongate member 130, and/or the outer sheath 110 (e.g., FIGS. 14-15). In some embodiments, the expandable framework 210 may be angled and/or oriented at an oblique angle relative to central longitudinal axis of the delivery device, the inner elongate member 130, and/or the outer sheath 110.

In at least some embodiments, the inner elongate member 130 may include a tether release element 196 configured to sever the tether 140, as seen in FIG. 19. In one example, the tether release element 196 may include a push button having a cutting element or blade disposed at and/or fixed to an opposing end of the push button. When the user is satisfied with the positioning of the implant 200, the tether release element 196 may be actuated to sever the tether 140, thereby releasing the implant 200 from the delivery device as described herein. Other configurations of the tether release element 196 are also contemplated, including but not limited to, an axial slider, a rotating knob, a scissors-like cutter, an automated release system, etc.

The materials that can be used for the various components of the system 100 and the implant 200, and the various elements thereof, disclosed herein may include those commonly associated with medical devices. For simplicity purposes, the following discussion makes reference to the system 100 and the implant 200. However, this is not intended to limit the devices and methods described herein, as the discussion may be applied to other elements, members, components, or devices disclosed herein, such as, but not limited to, the delivery device, the outer sheath, the inner elongate member, the tether, the release mechanism, the cutting blade, the adjustment element, the expandable framework, the anchor members, the proximal hub, the distal hub, the pin, the cam member, the occlusive element, and/or elements or components thereof.

In some embodiments, the system 100 and the implant 200, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the system 100 and the implant 200, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system 100 and the implant 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system 100 and the implant 200 to achieve the same result.

In some embodiments, a degree of Magnetic Resonance Imaging (Mill) compatibility is imparted into the system 100 and the implant 200 and/or other elements disclosed herein. For example, the system 100 and the implant 200, and/or components or portions thereof, may be made of a material that does not substantially distort the image and create substantial artifacts (i.e., gaps in the image). Certain ferromagnetic materials, for example, may not be suitable because they may create artifacts in an MM image. The system 100 and the implant 200, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system 100 and the implant 200 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system 100 and the implant 200 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni-Co-Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the system 100 and the implant 200 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A system for occluding a left atrial appendage, comprising:
 a delivery device including an outer sheath and an inner elongate member slidably disposed within a lumen of the outer sheath;
 an implant configured to occlude the left atrial appendage comprising:
  an expandable framework configured to shift between a collapsed configuration when disposed within the outer sheath and an expanded configuration when disposed outside of the outer sheath, wherein the expandable framework includes an attachment point configured to releasably secure the expandable framework to the delivery device; and
  an occlusive element disposed on a proximal portion of the expandable framework, wherein the occlusive element covers the attachment point, the occlusive element defining a proximalmost surface of the implant across an entirety of the implant;
  wherein the attachment point includes a cam member extending laterally across a proximal hub of the expandable framework and having a convex distal facing surface defined by an axis oriented perpendicular to the cam member, the cam member including a convex first lateral shoulder and a convex second lateral shoulder forming a channel in the convex distal facing surface of the cam member; and a tether extending longitudinally within a lumen of the inner elongate member, the tether engaging the attachment point in a delivery configuration;

wherein the tether passes through the occlusive element and extends around the convex distal facing surface of the cam member within the channel formed in the convex distal facing surface in the delivery configuration.

2. The system of claim 1, wherein the tether passes through the occlusive element twice in the delivery configuration.

3. The system of claim 1, wherein the tether is disengaged from the attachment point in a released configuration.

4. The system of claim 1, further comprising a release mechanism disposed within the lumen of the inner elongate member, wherein the release mechanism is configured to sever the tether within the lumen of the inner elongate member.

5. The system of claim 4, wherein the release mechanism includes a cutting blade disposed within the inner elongate member.

6. The system of claim 4, further comprising a turnstile movably engaged with a proximal end of the inner elongate member.

7. The system of claim 1, wherein
the cam member is configured to cooperate with a distal end of the inner elongate member.

8. The system of claim 7, wherein axial translation of the tether is configured to angle the expandable framework relative to a central longitudinal axis of the delivery device.

9. The system of claim 1, further including a plurality of anchor members configured to secure the implant to tissue within the left atrial appendage.

10. The system of claim 1, wherein the occlusive element includes a porous mesh.

* * * * *